US008246983B2

(12) United States Patent
O'Halloran et al.

(10) Patent No.: US 8,246,983 B2
(45) Date of Patent: Aug. 21, 2012

(54) ENCAPSULATED ARSENIC DRUGS

(75) Inventors: Thomas O'Halloran, Chicago, IL (US); Haimei Chen, Evanston, IL (US)

(73) Assignee: Northwestern University, Evarston, IL (US)

( * ) Notice: Subject to any disclaimer, the term of this patent is extended or adjusted under 35 U.S.C. 154(b) by 1079 days.

(21) Appl. No.: 11/515,711

(22) Filed: Sep. 5, 2006

(65) Prior Publication Data
US 2007/0065498 A1 Mar. 22, 2007

Related U.S. Application Data

(60) Provisional application No. 60/713,672, filed on Sep. 2, 2005.

(51) Int. Cl.
*A61K 9/127* (2006.01)
(52) U.S. Cl. .................. 424/450; 424/623
(58) Field of Classification Search .......... 424/450, 424/623
See application file for complete search history.

(56) References Cited

U.S. PATENT DOCUMENTS

| | | | | |
|---|---|---|---|---|
| 3,660,183 | A * | 5/1972 | Knowles et al. | 149/21 |
| 3,676,475 | A * | 7/1972 | Drinkard et al. | 556/7 |
| 5,008,050 | A | 4/1991 | Cullis et al. | |
| 5,620,689 | A * | 4/1997 | Allen et al. | 424/178.1 |
| 6,875,451 | B2 | 4/2005 | Ellison et al. | |
| 2002/0001629 | A1 * | 1/2002 | Voellmy | 424/620 |
| 2002/0183385 | A1 * | 12/2002 | Ellison et al. | 514/504 |
| 2003/0082154 | A1 * | 5/2003 | Leamon | 424/93.21 |
| 2003/0091621 | A1 * | 5/2003 | Tardi et al. | 424/450 |
| 2003/0147945 | A1 * | 8/2003 | Tardi et al. | 424/450 |
| 2004/0071768 | A1 * | 4/2004 | Sarris et al. | 424/450 |
| 2004/0253302 | A1 | 12/2004 | Sarris et al. | |
| 2007/0010700 | A1 * | 1/2007 | Bensmann et al. | 588/1 |

OTHER PUBLICATIONS

Voskoglou-Nomikos et al , Clinical Cancer Research, vol. 9, Sep. 15, 2003, pp. 4227-4239.*
Allen et al. 2004, "Drug Delivery Systems: Entering the Mainstream", Science 303: 1818-1822.
Bandak et al. 1999, "Pharmacological studies of cisplatin encapsulated in long-circulating liposomes in mouse tumor models", Anticancer Drugs 10: 911-920.
Burger et al. 2002, "Nanocapsules: lipid-coated aggregates of cisplatin with high cytotoxicity", Nature Medicine 8: 81-84.
Chen 1996, "In Vitro Studies on Cellular and Molecular Mechanisms of Arsenic Trioxide (As2O3) in the Treatment of Acute Promyelocytic Leukemia: As2O3 Induces NB4 Cell Apoptosis With Downregulation of Bcl-2 Expression and Modulation of PML-RARdPML Proteins", Blood 88: 1052-1061.
Dhubhghaill et al., 1991, "The Structure and Reactivity of Arsenic Compounds: Biological Activity and Drug Design", Structure and Bonding 78: 129-190.
Fenske et al., "Ionophore-mediated Uptake of Ciprofloxacin and Vincristine Into Large Unilamellar Vesicles exhibiting Transmembrane Ion Gradients" 1998 Biochimica Biophisica Acta. vol. 1414 pp. 188-204.
Haller 1975, "Therapeutic Mule: The Use of Arsenic in the Nineteenth Century Materia Medica", Pharm. Hist. 17: 87-100.
Haran et al. 1993, "Transmembrane ammonium sulfate gradients in liposomes produce efficient and stable entrapment of amphipathic weak bases", Biochim. Biophys. Acta 1151: 201-215.

(Continued)

*Primary Examiner* — Gollamudi Kishore
(74) *Attorney, Agent, or Firm* — Casimir Jones, S.C.

(57) ABSTRACT

The present invention relates to methods and compositions for the treatment of cancer and for research and analysis of cancer. In particular, the present invention provides encapsulated arsenic anti-cancer compositions with improved properties.

8 Claims, 12 Drawing Sheets

M , any transitional metal ion. In this example, M is the Ni(II) ion
A , any conjugate base of a weak acid. In this example, A is the acetate ion

OTHER PUBLICATIONS

Jia et al. 2001, "Arsenic trioxide induces multiple myeloma cell apoptosis via disruption of mitochondrial transmembrane potentials and activation of caspase-3", Chin. Med. J. 114:19-24.

Kallinteri et al. 2004, "Aresenic Trioxide Liposomes: Encapsulation Efficiency and in Vitro Stability", J. Liposome Res. 14: 27-38.

Loehr et al. 1968, "Raman Spectra and Structures of Arsenious Acid and Arsenities in Aqueous Solution", Inorg. Chem. 7: 1708-1714.

Lu et al. 2002, "Current Study of APL Treatment in China", International Journal of Hematology 76: 316-318.

Mayer et al. 1986, "Uptake of adriamycin into large unilamellar vesicles in response to a pH gradient", Biochim. Biophys. Acta 857: 123-126.

Mayer et al. 1986, "Techniques for Encapsulating Bioactive Agents Into Liposomes", Chem. Phys. Lipids 40: 333-345.

Mayer et al. 1990, "Characterization of liposomal systems containing doxorubicin entrapped in response to pH gradients", Biochim. Biophys. Acta 1025: 143-151.

Mervis 1996, "Ancient Remedy Performs New Tricks", Science 273: 578.

New 1990, "Liposomes—a practical approach." Oxford University Press.

Newman et al. 1999, "Comparative pharmacokinetics, tissue distribution, and therapeutic effectiveness of cisplatin encapsulated in long-circulating, pegylated liposomes (SPI-077) in tumor-bearing mice", Cancer Chemotherapy and Pharmacology 43: 1-7.

Roboz et al. 2000, "Arsenic trioxide induces dose- and time-dependent apoptosis of endothelium and may exert an antileukemic effect via inhibition of angiogenesis", Blood 96: 1525-1530.

Soignet et al., 1998, "Complete Remission After Treatment of Acute Promyelocytic Leukemia With Arsenic Trioxide", N. Engl. J. Med. 339: 1341-1348.

Steerenberg et al. 1988, "Liposomes as drug carrier system for cis-diamminedichloroplatinum (II)", Cancer Chemotherapy and Pharmacology, 21: 299-307.

Sun et al. 1992 Chinese Journal of Integrated Traditional and Western Medicine 12: 170-171.

Yatvin et al. 1981, "Selective Delivery of Liposome-associated cis-Dichlorodiammineplatinum(II) by Heat and Its Influence on Tumor Drug Uptake and Growth", Cancer Res. 41: 1602-1607.

* cited by examiner

Arsenite

Arsenous acid

Thioarsenous acid

Arsenate

Methylarsinic acid

Dimethylarsinic acid cisplatin

Aqua-cisplatin

Tetrathiomolybate

M , any transitional metal ion. In this example, M is the Ni(II) ion
A , any conjugate base of a weak acid. In this example, A is the acetate ion (A)

↓ Arsenic loading (B)

ENCAPSULATED ARSENIC DRUGS

This application claims priority to U.S. Provisional Patent Application Ser. No. 60/713,672, filed Sep. 2, 2005, the disclosure of which is herein incorporated by reference in its entirety.

The present invention was made, in part, under funds from NIH grant nos. R01 GM38784 and R01 GM54111. The government may have certain rights in the invention.

FIELD OF THE INVENTION

The present invention relates to methods and compositions for the treatment of cancer and for research and analysis of cancer. In particular, the present invention provides encapsulated arsenic anti-cancer compositions with improved properties.

BACKGROUND

Each year, nearly 27,000 adults and more than 2,000 children in the United States learn that they have leukemia. Leukemia is characterized by large numbers of abnormal blood cells, generally white blood cells.

There are several types of leukemia. Leukemia is either acute or chronic. In acute leukemia, the abnormal blood cells are blasts that remain very immature and cannot carry out their normal functions. The number of blasts increases rapidly, and the disease gets worse quickly. In chronic leukemia, some blast cells are present, but in general, these cells are more mature and can carry out some of their normal functions. Also, the number of blasts increases less rapidly than in acute leukemia. As a result, chronic leukemia gets worse gradually.

Leukemia can arise in either of the two main types of white blood cells—lymphoid cells or myeloid cells. When leukemia affects lymphoid cells, it is called lymphocytic leukemia. When myeloid cells are affected, the disease is called myeloid or myelogenous leukemia. Acute lymphocytic leukemia (ALL) is the most common type of leukemia in young children. This disease also affects adults, especially those age 65 and older. Acute myeloid leukemia (AML) occurs in both adults and children. This type of leukemia is sometimes called acute nonlymphocytic leukemia (ANLL). Chronic lymphocytic leukemia (CLL) most often affects adults over the age of 55. It sometimes occurs in younger adults, but it almost never affects children. Chronic myeloid leukemia (CML) occurs mainly in adults. A very small number of children also develop this disease. Hairy cell leukemia is an uncommon type of chronic leukemia.

Common symptoms of leukemia include fever, chills, and other flu-like symptoms, weakness and fatigue, frequent infections, loss of appetite and/or weight, swollen or tender lymph nodes, liver, or spleen, easy bleeding or bruising, small red spots (called petechiae) under the skin, swollen or bleeding gums, sweating, especially at night; and/or bone or joint pain.

Treatment varies with the type of leukemia and the age and medical status of the patient. Treatment options include chemotherapy, radiation, bone marrow transplantation, and biological therapy such as interferon.

Survival rate varies based on the type and stage of leukemia as well as the patient's age and health. Even with new advances in care, patients with many types of leukemia continue to have low long-term survival rates. What is needed are improved treatment methods.

SUMMARY OF THE INVENTION

The present invention relates to methods and compositions for the treatment of cancer and for research and analysis of cancer. In particular, the present invention provides encapsulated arsenic anti-cancer compositions with improved properties.

Accordingly, in some embodiments, the present invention provides a composition comprising a liposome, wherein the liposome encapsulates a metal and an amphiphilic drug. In some embodiments, the amphiphilic drug is an arsenic-containing drug (e.g., arsenite, arsenic trioxide, arsenic sulfide, arsenate, methylarsinic acid or dimthylarsinic acid). In some embodiments, the metal is Ni, Co, Cu, Zn, Mn, Fe, Pb, V, Ti, Cr, Pt, Rh, Ru, Mo, Hg, Ag, Gd, Cd or Pd. In preferred embodiments, the liposome is stable under physiological conditions but releases the drug at low pH. In certain embodiments, the liposome further comprises a second amphiphilic drug. In some embodiments, the liposome comprises a composition having the formula $M_n(AsX_3)_m$, wherein X is O, OH, S, SH, Se, or SeH, M is a metal ion, n is 1, 2, or 3 and m is 1, 2, or 3. In some embodiments, the liposome further comprises a targeting ligand. In preferred embodiments, the targeting ligand is an antibody (e.g., Rituxan, Campath-1H, HM1.24, HER2, Anti-CD38, HuM195, or HP67.6), folic acid, retinoic acid, a peptide, an estrogen analog, transferrin, or granulocyte-macrophage colony stimulating factor. A variety of other targeting ligands that find use with the present invention are known in the art.

The present invention further provides a method, comprising, providing a liposome; combining the liposome with a metal ion under conditions such that the metal ion is encapsulated in the liposome; and contacting the liposome comprising the encapsulated metal ion with an amphiphilic drug under conditions such that the drug is encapsulated in the liposome. In some embodiments, the amphiphilic drug is an arsenic-containing drug (e.g., arsenite, arsenic trioxide, arsenic sulfide, arsenate, methylarsinic acid or dimthylarsinic acid). In some embodiments, the metal is Ni, Co, Cu, Zn, Mn, Fe, Pb, V, Ti, Cr, Pt, Rh, Ru, Mo, Hg, Ag, Gd, Cd or Pd. In preferred embodiments, the liposome is stable under physiological conditions but releases the drug at low pH, temperature change or contact with a second liposome comprising a fluid liposome with a lower gel to crystal transition temperature than the liposome. In certain embodiments, the liposome further comprises a second amphiphilic drug. In some embodiments, the liposome comprises a composition having the formula $M_n(AsX_3)_m$, wherein X is O, OH, S, SH, Se, or SeH, M is a metal ion, n is 1, 2, or 3 and m is 1, 2, or 3. In some embodiments, the liposome further comprises a targeting ligand. In preferred embodiments, the targeting ligand is an antibody (e.g., Rituxan, Campath-1H, HM1.24, HER2, Anti-CD38, HuM195, or HP67.6), folic acid, retinoic acid, a peptide, an estrogen analog, transferrin, or granulocyte-macrophage colony stimulating factor.

The present invention additionally provides a method of treating or analyzing a cancer, comprising administering the liposomal composition comprising an amphiphilic drug described herein to a subject diagnosed with or suspected of having cancer (e.g., Lymphoma, Multiple Myeloma (MM), Acute Promyelocytic Leukemia (APL), Acute Myeloid Leukemia (AML), Chronic Lymphocytic Leukemia (CLL), breast cancer, ovarian cancer, pancreatic cancer, bladder cancer, lung cancer, liver cancer, brain cancer, neck cancer, colorectal cancer, etc.). In some embodiments, the cancer is analyzed following treatment to determine the effect of the compositions on the cancer.

Thus, the present invention describes a novel and widely applicable method of efficient and rapid loading of arsenic drugs at high density into liposomes. The method yields robust As-loaded liposomes or other lipid complexes that can retain the drug under physiological conditions. These arsenic loaded liposomes are stable in serum conditions but release their drug contents in lower pH environments, such as in the intracellular endosomes. The loading mechanism can be described as a nano-pump. For example, during one cycle, the external neutral arsenic compound, for example, $As(OH)_3$, diffuses across the membrane to form insoluble metal arsenite complexes internally. Protons are released and associate with the basic acetate anions. The resulting weak acid (HAc) then diffuses out of the liposome in exchange for $As(OH)_3$, leading to significant accumulation of arsenic inside liposomes. Both the formation of insoluble metal arsenite complexes and the efflux of acetic acid drive arsenic uptake.

The present invention also provides a novel way to transport the arsenic reactants into the liposome. This produces various salts of arsenous acids in nanoparticle-form. These are sequestered in a biocompatible vehicle to be delivered to cancer targets or other targets.

The encapsulation methods of the present invention are applicable for other amphiphatic agents. Preferably, a therapeutic agent is one that is able to diffuse across lipid- or polymer-membranes at a reasonable rate and which is capable of coordinating with a metal encapsulated within the liposome in a prior step. Agents that are capable of coordination with a transition metal typically comprise of coordination sites such as hydroxyl, thiols, acetylenes, amines or other suitable groups capable of donating electrons to the transition metal thereby forming a complex with the metal.

The drug loading method is applicable for multi-drug co-encapsulation into one vesicle, provided that one or more therapeutic agents are first passively encapsulated inside liposomes and the second therapeutic agent is added to the external solution of said liposomes and is thus actively loaded. Two or more drugs, such as inorganic drugs of arsenic, cisplatin (cis-diaminedichloroplatinum) and its hydrolyzed products, and tetrathiomolybate and its hydrolyzed products, and organic drugs of retinoic acid and nucleoside analogues, 8-chloro- or 8-$NH_2$-adenosine, et al. can be incorporated into liposomes by combining passive and active methods of loading.

DEFINITIONS

Figure 1:
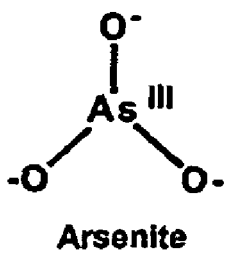
FIG. 1 shows structures of arsenic, platinum and molybdenum drugs used in some embodiments of the present invention.
Figure 1:
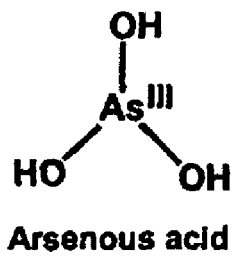
Figure 1:
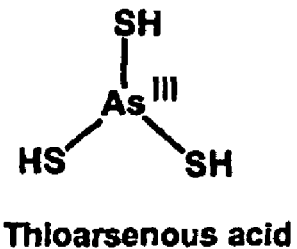
Figure 1:
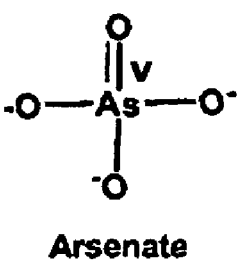
Figure 1:
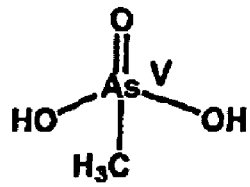
Figure 1:
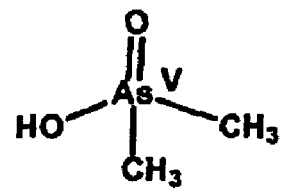
Figure 1:
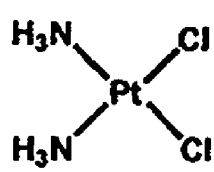
Figure 1:
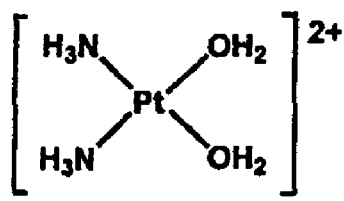
Figure 1:
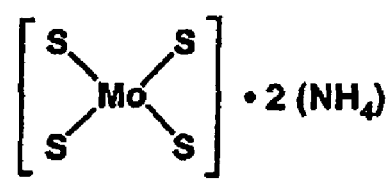

To facilitate an understanding of the present invention, a number of terms and phrases are defined below:

As used herein, the term "subject" refers to any animal (e.g., a mammal), including, but not limited to, humans, non-human primates, rodents, and the like, which is to be the recipient of a particular treatment. Typically, the terms "subject" and "patient" are used interchangeably herein in reference to a human subject.

As used herein, the term "subject suspected of having cancer" refers to a subject that presents one or more symptoms indicative of a cancer or is being screened for a cancer (e.g., during a routine physical). A subject suspected of having cancer may also have one or more risk factors. A subject suspected of having cancer has generally not been tested for cancer. However, a "subject suspected of having cancer" encompasses an individual who has received a preliminary diagnosis but for whom a confirmatory test has not been done or for whom the stage of cancer is not known. The term further includes people who once had cancer (e.g., an individual in remission). A "subject suspected of having cancer" is sometimes diagnosed with cancer and is sometimes found to not have cancer.

As used herein, the term "subject diagnosed with a cancer" refers to a subject who has been tested and found to have cancerous cells. The cancer may be diagnosed using any suitable method, including but not limited to, biopsy, x-ray, and blood test. A "preliminary diagnosis" is one based only on visual and antigen tests.

As used herein, the term "initial diagnosis" refers to a test result of initial cancer diagnosis that reveals the presence or absence of cancerous cells.

As used herein, the term "post surgical tumor tissue" refers to cancerous tissue that has been removed from a subject (e.g., during surgery).

As used herein, the term "subject at risk for cancer" refers to a subject with one or more risk factors for developing a specific cancer. Risk factors include, but are not limited to, gender, age, genetic predisposition, environmental expose, and previous incidents of cancer, preexisting non-cancer diseases, and lifestyle.

The terms "test compound" and "candidate compound" refer to any chemical entity, pharmaceutical, drug, and the like that is a candidate for use to treat or prevent a disease, illness, sickness, or disorder of bodily function (e.g., cancer). Test compounds comprise both known and potential therapeutic compounds. A test compound can be determined to be therapeutic by screening using the screening methods of the present invention.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Environmental samples include environmental material such as surface matter, soil, water and industrial samples. Such examples are not however to be construed as limiting the sample types applicable to the present invention.

As used herein, the terms "anticancer agent," "conventional anticancer agent," or "cancer therapeutic drug" refer to any therapeutic agents (e.g., chemotherapeutic compounds and/or molecular therapeutic compounds), radiation therapies, or surgical interventions, used in the treatment of cancer (e.g., in mammals).

As used herein, the terms "drug" and "chemotherapeutic agent" refer to pharmacologically active molecules that are used to diagnose, treat, or prevent diseases or pathological conditions in a physiological system (e.g., a subject, or in vivo, in vitro, or ex vivo cells, tissues, and organs). Drugs act by altering the physiology of a living organism, tissue, cell, or in vitro system to which the drug has been administered. It is intended that the terms "drug" and "chemotherapeutic agent" encompass anti-hyperproliferative and antineoplastic compounds as well as other biologically therapeutic compounds.

The term "derivative" of a compound, as used herein, refers to a chemically modified compound wherein the chemical modification takes place either at a functional group of the compound, aromatic ring, or carbon backbone. Such derivatives include esters of alcohol-containing compounds, esters of carboxy-containing compounds, amides of amine-containing compounds, amides of carboxy-containing compounds, imines of amino-containing compounds, acetals of aldehyde-containing compounds, ketals of carbonyl-containing compounds, and the like.

As used herein, the term "pharmaceutically acceptable salt" refers to any salt (e.g., obtained by reaction with an acid or a base) of a compound of the present invention that is physiologically tolerated in the target subject (e.g., a mammalian subject, and/or in vivo or ex vivo, cells, tissues, or organs). "Salts" of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, sulfonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

Examples of bases include, but are not limited to, alkali metal (e.g., sodium) hydroxides, alkaline earth metal (e.g., magnesium) hydroxides, ammonia, and compounds of formula $NW_4^+$, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, chloride, bromide, iodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like. For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

An "effective amount" is an amount sufficient to effect beneficial or desired results. An effective amount can be administered in one or more administrations.

As used herein, the term "administration" refers to the act of giving a drug, prodrug, or other agent, or therapeutic treatment (e.g., radiation therapy) to a physiological system (e.g., a subject or in vivo, in vitro, or ex vivo cells, tissues, and organs). Exemplary routes of administration to the human body can be through the eyes (opthalmic), mouth (oral), skin (transdermal), nose (nasal), lungs (inhalant), oral mucosa (buccal), ear, by injection (e.g., intravenously, subcutaneously, intratumorally, intraperitoneally, etc.) and the like. "Coadministration" refers to administration of more than one chemical agent or therapeutic treatment to a physiological system (e.g., a subject or in vivo, in vitro, or ex vivo cells, tissues, and organs). "Coadministration" of the respective chemical agents and therapeutic treatments may be concurrent, or in any temporal order or physical combination.

DETAILED DESCRIPTION OF THE INVENTION

The present invention relates to methods and compositions for the treatment of cancer and for research and analysis of cancer. In particular, the present invention provides encapsulated arsenic anti-cancer compositions with improved properties.

Arsenic in Medicine

Arsenic was first used by Greek and Chinese healers more than 2,000 years ago to treat various diseases from syphilis to cancers. Arsenic-containing drugs played a central role in the development of modern pharmacology. In the late eighteenth century, Fowler's solution (a solution containing 1% potassium arsenite) was originally used to treat periodic fever, and later, a large variety of diseases including chronic myelogenous leukemia (CML) (Haller, J. S. Pharm. Hist. (1975) 17: 87-100). In 1910, Salvarsan (Arsphenamine), an organic arsenic-based drug, was disclosed to be effective in treating tuberculosis and syphilis (Ehrlich, P., Bertheim, A. US 986148 (1911)). Other organic arsenicals, such as Malarsoprol, are still used today to treat trypanosomiasis (an advanced sleeping sickness) (Dhubhghaill, O. M. N. et al. Structure and Bonding (1991) 78: 129-190).

In traditional Chinese medicine, arsenous acid or arsenic trioxide paste has been used to treat tooth marrow diseases, psoriasis, syphilis and rheumatosis. In the 1970's, arsenic trioxide was applied to treat acute promyelocytic leukemia (APL) in China (Sun, H. D. et al. Chin. J. Integrat. Trad. Clin. West. Med. (1992) 12: 170-171; Mervis, J. Science (1996) 273: 578; Chen, G.-Q. Blood (1996) 88: 1052-1061). Arsenic trioxide (TRISONEX) is now in phase III clinical trials for various leukemias including Acute Promyelocytic Leukemia (APL) and in phase I/II for relapsed/refractory multiple myeloma (MM) in China, Japan, Europe and the United States (Soignet, S. L. et al. N. Engl. J. Med. (1998) 339: 1341-1348; Jia, P. et al. Chin. Med. J. (2001) 114:19-24). Owing to a synergistic effect with retinoic acid, arsenic trioxide is often combined with retinoic acid for improved treatment of APL and MM.

Mineral forms of tetra-arsenic tetrasulfide ($As_4S_4$) and diarsenic trisulfide ($As_2S_3$), have been major components in other traditional medicines in China for more than 1500 years, such as realgar and orpiment. Recently, both $As_4S_4$ and $As_2S_3$ have been used in clinical trials in China for treatment of APL (Lu, D. et al. International Journal of Hematology (2002) 76: 316-318).

The salts of arsenous acid, such as sodium arsenite ($NaAsO_2$), potassium arsenite (KAsO2), calcium arsenite ($Ca(HAsO_3)$), copper arsenite ($CuHAsO_3$, Scheele's green), copper acetoarsenite ($3Cu(AsO_2)_2 \cdot Cu(O_2CCH_3)_2$, Paris green), and lead arsenite ($Pb(HAsO_3)$), and the salts of arsenic acid, such as calcium arsenate ($Ca_3(AsO_4)_2$, and lead arsenate ($Pb_3(AsO_4)_2$) are poisonous. They have been used as anticancer agents (sodium arsenite and potassium arsenite) and in viticulture as insecticides, weed killers, germicide and rodenticides, in preserving hides and in the manufacturer of soap and antiseptics (The Merck Index, $10^{th}$, 1983; Columbia Encyclopedia, $6^{th}$, 2004).

Despite its excellent therapy, arsenic compounds have a variety of widely appreciated toxic effects, including reduced viability of reticulo-endothelial cells (Roboz, G. J. et al. Blood (2000) 96: 1525-1530). Give this toxicity arsenic drugs must be given at low concentrations, which are ineffective in the treatment of many cancers. There is a need for methods for reducing the toxic side effects of arsenic while retaining its valuable therapeutic effect.

Liposomes as Drug Carriers

Liposomes are microscopic lipid bilayer vesicles and have been widely used as carriers for a variety of agents such as drugs, cosmetics, diagnostic reagents, and genetic materials (New, R. Liposomes—a practical approach. Oxford University Press. 1990). Liposomes can encapsulate water-soluble agents in their aqueous cavities, or carry lipid-soluble agents within the membrane itself. Encapsulation of pharmaceuticals in liposomes can reduce drug side effects, improve pharmacokinetics of delivery to a target site, and improve the therapeutic index of a drug.

Loading of drugs into liposomes is an important step in the development of drug delivery methods. Achieving maximum amount of drug accumulation inside liposomes, improving stability, reducing leakage, and realization of biocompatible-triggered release of drugs are major long-term goals. The loading methods vary depending on both physical and chemical properties of the drugs. In general, lipid-soluble drugs are easier to load because they easily incorporate into the lipid bilayer during liposome formation. Water-soluble drugs are also readily loaded because they interact with the polar head group of phospholipids facing the interior of liposomes and are therefore sequestered inside the liposomes. Amphiphatic compounds, on the other hand, are the most difficult to retain inside liposomes, as they can rapidly permeate through lipid bilayers.

The simplest method of drug loading is a passive entrapment of drugs in liposomes by hydration of the dry lipid film in an aqueous drug solution (Mayer, L. D. et al. Chem. Phys. Lipids (1986) 40: 333-345). The loading efficiency depends on the permeability of the drug across the membrane or the ease of the drug to escape from liposomes. This method is suitable for water-soluble drugs but not lipid-soluble ones.

For amphiphatic drugs, such as Doxorubicin (DXR), the previously reported-encapsulation method is loading of the drug into liposomes in response to a pH gradient where the internal pH of the liposome is made lower than the external medium pH and drugs consequently diffuse into liposomes in their neutral forms and are entrapped inside as positively charged forms (Mayer, L. D. et al. Biochim. Biophys. Acta (1986) 857: 123-126; (1990) 1025: 143-151). This method appears to be reasonably efficient for loading, if not for the fact that it requires internal acidification and external concentration of strong base (KOH), both of which cause lipid hydrolysis. Also, the resulting liposome-drug vesicles are unstable. Stable entrapment of DXR has been later reported where ammonium sulfate was used as the intraliposomal medium and DXR consequently entered and formed an aggregated form with sulfate and was encapsulated inside liposomes (Haran, G. et al. Biochim. Biophys. Acta (1993) 1151: 201-215). This method has enabled the clinical use of DXR-loaded sterically-stabilized liposomes. It is today called DOXIL (doxorubicin HCl liposome injection). DOXIL has been approved for the treatment of AIDS-related Kaposi's sarcoma (the U.S. Food and Drug Administration, 1995), refractory ovarian cancer (the U.S. Food and Drug Administration, 1999), metastatic breast cancer in combination with cyclophosphamide (Europe, 2000), and refractory breast cancer (Europe and Canada, 2003) (Allen, T. M. et al. Science (2004) 303: 1818-1822).

Cisplatin (cis-diamminedichloroplatinum) is an anticancer drug used worldwide in the treatment of epithelial malignancies such as lung, head and neck, ovarian and testicular cancer. The approach of preparing less toxic, liposomal formulations has been studied that use a passive method of encapsulating cisplatin in liposomes by hydration of the dry lipid film in the cisplatin aqueous solution (Yatvin, M. B. et al. Cancer Res. (1981) 41: 1602-1607; Steerenberg, P. A. et al. Cancer Chemother. Pharmacol. (1988) 21: 299-307). Due to both the low water solubility and low lipophilicity of cisplatin, this method provides very low encapsulation efficiencies with a very low drug-to-lipid ratio which limits the bioavailability of cisplatin in the tumor and results in low cytoxicity (Bandak, S. et al. Anticancer drugs (1999) 10: 911-920; Newman, M. S. et al. Cancer Chemother. Pharmacol. (1999) 43: 1-7). Recently, a new method was developed by combining negatively charged phospholipids, such as 50% phosphatidylserine (PS), into the neutral phosphatidylcholine (PC). The negative head groups of PS lipids appear to interact with the positively charged aqualized-species of $[(NH_3)_2Pt(H_2O)_2]^{2+}$ and allow for efficient and stable aggregates of $\{(NH_3)_2Pt\}^{2+}$ within liposomes, leading to high cytotoxicity (Burger, K. N. J. et al. Nature Medicine (2002) 8: 81-84).

There is high demand for novel arsenic-based drugs that exhibit higher activities but lower toxic side effects than the solution of the mineral compounds. This can be realized by means of a lipid coating. Arsenic trioxide is an amphiphatic agent (soluble both in aqueous and hydrophobic phases), which makes liposomal formulation difficult. Previous attempts to prepare liposomal arsenic trioxide by hydration of lipid components in the concentrated aqueous solution of arsenic trioxide (Kallinteri, P. et al. J. Liposome Res. (2004) 14: 27-38) were met with limited success; the resulting Liposome-arsenic vesicles were unstable and suffered from substantial leakage of the drug within 24 hours. This significantly impaired the application of this method.

The present invention provides an unprecedented approach for loading arsenic drugs into liposomes and delivery of arsenic into specific tumor cells allowing for useful pharmaceutical preparations comprising liposomes containing arsenic drugs. The present invention creates a novel system that takes advantage of transmembrane gradients of transitional metal ion salts to obtain the efficient and stable loading of a weak acid-$H_3AsO_3$ into liposomes by forming nano-particles inside (miniralization). The formation of insoluble metal-arsenite complexes and the efflux of acetic acids (HAc) are the two driving forces for the efficient accumulation of arsenic inside liposomes. Both metal cation and anion (e.g., acetate, famate, lactate and hydroxyacetate) have important roles in drug loading and release.

In some embodiments, the present invention provides methods for loading arsenic into liposomes, comprising: preparing liposomes comprising an encapsulated metal ion and adding an agent such as arsenite, arsenic trioxide, arsenic sulfide, arsenate, methylarsinic acid and dimethylarsinic acid and other arsenic analogues.

The present invention further provides methods of synthesis of several new compositions of matter. In some embodiments, they are liposomes comprising $M_n(AsX_3)_m$ particles, where X=O, OH, S, SH, Se, SeH; M=metal ion; n=1, 2, 3; m=1, 2, 3. Methods include selecting a metal cation or an anion for encapsulation in a liposome to achieve desired retention of an encapsulated agent. The efficiency and stability of loading and release of drugs can be modified and controlled by employing different cations and anions. Screening for activity can be conducted to select optimized conditions as desired.

The metal ions for use in this invention include, but are not limited to, transitional metals of the group 1B, 2B, 3B, 4B, 5B, 6B, 7B and 8B elements (groups 3-12), and the basic metals from groups of IIIA and IVA and VA. Preferred metals may be selected from one or more of Ni, Co, Cu, Zn, Mn, Fe, Pb, V, Ti, Cr, Pt, Rh, Ru, Mo, Hg, Ag, Gd, Cd and Pd. The metal ions may include their radical reactive isotopes, such as $^{71}$As, $^{72}$As, $^{73}$As, $^{74}$As, $^{76}$As, $^{77}$As, $^{57}$Ni, $^{65}$Ni, $^{66}$Ni, $^{55}$Co, $^{61}$Cu, $^{62}$Cu, $^{64}$Cu, $^{66}$Cu, $^{67}$Cu, $^{72}$Zn, $^{51}$Mn, $^{52m}$Mn, $^{99}$Mo, $^{99m}$Tc, $^{203}$Pb, $^{63}$Ga, $^{66}$Ga, $^{67}$Ga, $^{111}$In, $^{97}$Ru, $^{52}$Fe, $^{51}$Cr, $^{186}$Re, $^{188}$Re, $^{90}$Y, $^{169}$Er, $^{117m}$Sn, $^{121}$Sn, $^{127}$Te, $^{142}$Pr, $^{143}$Pr, $^{198}$Au, $^{199}$Au, $^{149}$Tb, $^{161}$Tb, $^{109}$Pd, $^{165}$Dy, $^{143}$Pm, $^{151}$Pm, $^{157}$Gd, $^{166}$Ho, $^{172}$Tm, $^{169}$Yb, $^{175}$yb, $^{177}$Lu, $^{105}$Rh, $^{111}$Ag, $^{89}$Zr, $^{82m}$Rb, $^{118}$Sb, $^{193}$Pt, $^{195m}$Pt. This present invention is not limited to the encapsulation of arsenic compounds. The encapsulation methods of the present invention further are applicable to the encapsulation of other bioactive agents for the therapy or diagnosis of disease.

The present invention provides encapsulation methods that are applicable for other amphiphatic agents. Preferably, a therapeutic agent is one that is able to diffuse across lipid- or polymer-membranes at a reasonable rate and which is capable of coordinating with a metal encapsulated within the liposome in a prior step. Agents that are capable of coordination with a transition metal typically comprise of coordination sites such as hydroxyl, thiols, acetylenes, amines or other suitable groups capable of donating electrons to the transition metal thereby forming a complex with the metal.

The present invention provides encapsulation methods that are applicable for multi-drug co-encapsulation into one vesicle, provided that one or more therapeutic agents are first passively encapsulated inside liposomes and the second therapeutic agent is added to the external solution of said liposomes and is thus actively loaded. Two or more drugs, such as inorganic drugs of arsenic, cisplatin (cis-diaminedichloroplatinum) and its hydrolyzed products, and tetrathiomolybate and its hydrolyzed products, and organic drugs of retinoic acid and nucleoside analogues, 8-chloro- or 8-$NH_2$-adenosine, etc. can be incorporated into liposomes by combining passive and active methods of loading.

The novel liposomal $M_n(AsX_3)_m$ nano-particles of the present invention have a long shelf life (e.g., greater than a day, week, month, 6 months, year, etc.). This meets the pharmaceutical requirements for clinical use. No "bedside" preparation of liposomal arsenic drugs is required immediately before patient treatment and the formulation is ready for injection.

The novel $M_n(AsX3)_m$ nano-particles of the present invention have a specialized feature: they will dissolve in low pH environments, like those found within compartments of cancerous cells. The arsenic release from liposomal $M_n(AsX_3)_m$ nano-particles is triggered by lowering pH values. The accurate controlled release of arsenic can be realized by making use of different degree of acidic sensitivity of different $M_n(AsX_3)_m$ complexes.

The present invention also provides methods of arsenic release, either triggered by temperature, pH or by employing liposomes comprised of the fluid lipids with lower gel-to-crystal transitional temperatures ($T_m$), such as dioleoylphosphatidylcholine (DOPC) ($T_m$=−20° C.), dioleoylphosphatidylglycerol (DOPG) ($T_m$=−18° C.), palmitoyl-oleoyl-phosphatidylcholine POPC ($T_m$=−2° C.), dilauroyl-phosphatidylcholine (DLPC) ($T_m$=−1° C.), dimyristoyl-phosphatidylcholine (DMPC) ($T_m$=23° C.), egg-phosphatidylcoline egg-PC ($T_m$=37° C.).

The present invention further provides a method of preparation of arsenic-encapsulated liposomes with a broad spectrum of types, sizes, and composition, including sterically-stabilized liposomes, immunoliposomes, and sterically-stabilized immunoliposomes. The encapsules can be all types of vesicles, such as liposomes, lipid emulsions, micelles, and nano- or micro-spheres.

The present invention also provides methods of coupling liposomal $M_n(AsX_3)_m$ nano-particles to antibodies, such as Rituxan, and of evaluating cytotoxicity of conjugates on the human B-cell lymphoma SU-SHL-4. Such ligand-targeted liposomal $M_n(AsX_3)_m$ are effective therapeutics and exhibit lower toxicity as compared with the parent arsenic drugs.

The targeting antibodies applicable to this invention can be various types of antibodies, including, but not limited to, Rituxan, Campath-1H, HM1.24, HER2, Anti-CD38, HuM195, HP67.6. Non-antibody ligands include, for example, including, but not limited to, folate, retinoic acid, estrogen analogs such as galactosamine, Arg-Gly-Asp tripeptide (RGD), Asn-Gly-Arg (NGR), Octreotide, Granulocyte-macrophage colony-stimulating factor (GM-CSF), and proteins, such as transferrin are also suitable for use with the present invention.

The present invention further provides a method of preparing and using ligand-targeted liposomal $M_n(AsX_3)_m$ for treatment of various types of tumors, including, but not limited to, hematological tumors, such as Lymphoma, Multiple Myeloma (MM), Acute Promyelocytic Leukemia (APL), Acute Myeloid Leukemia (AML), Chronic Lymphocytic Leukemia (CLL), and solid tumors, such as breast, ovarian, pancreate, bladder, lung, liver, brain, neck, colorectal cancers, etc.

I. Lipid-Drug Complexes

Figure 3:
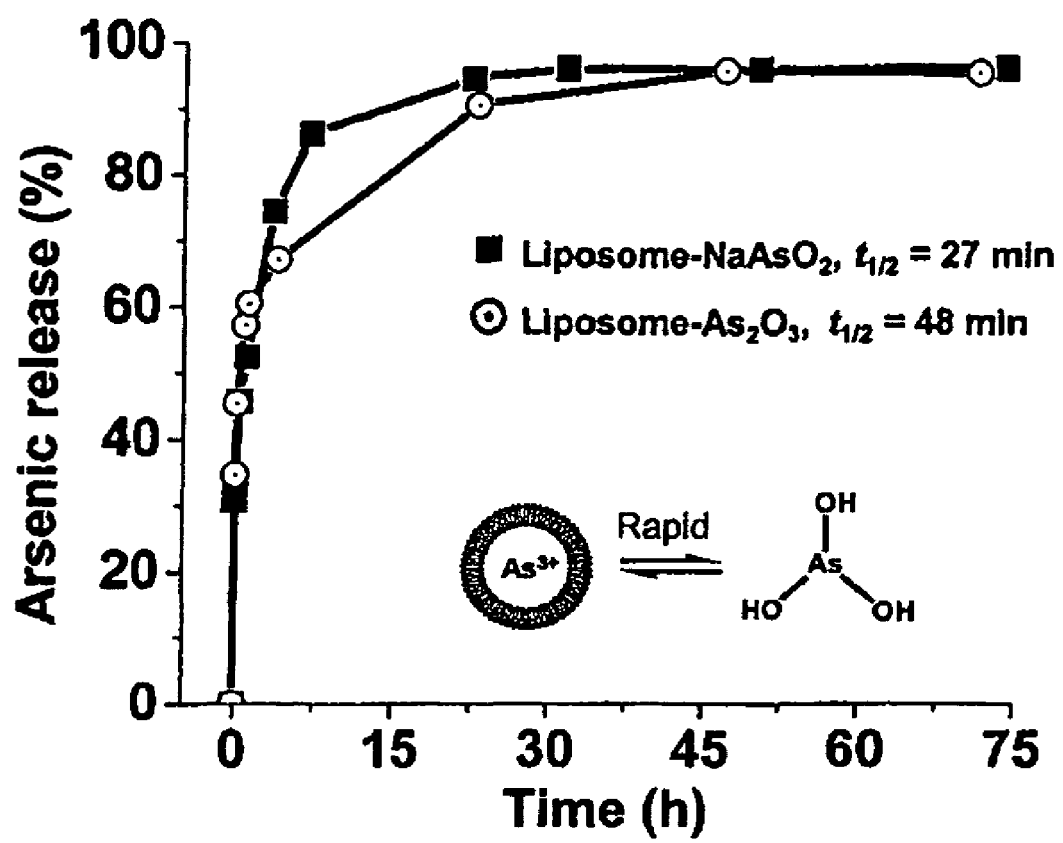
FIG. 3 shows that arsenous acids ($H_3AsO_3$) pass across liposome bilayers rapidly.

In neutral or acidic solutions, arsenic(III) species (FIG. 1) are primarily present as neutral $H_3AsO_3$ due to the $pK_a$ of 9.3 for $H_2AsO_3^{2-}$ (Loehr, T. M. et al. Inorg. Chem. (1968) 7: 1708-1714). $H_3AsO_3$ is soluble both in aqueous and hydrophobic phases and readily diffuses across the lipid membrane (Example 2 and FIG. 3). The passively encapsulated $H_3AsO_3$ (150 mM) leaks out after 24 h at 4° C. with half-time <50 min (FIG. 3). It is difficult to realize the stable retention and controlled release of arsenic using passive methods in the encapsulation of arsenic(III) drug under physiological conditions.

Figure 2:
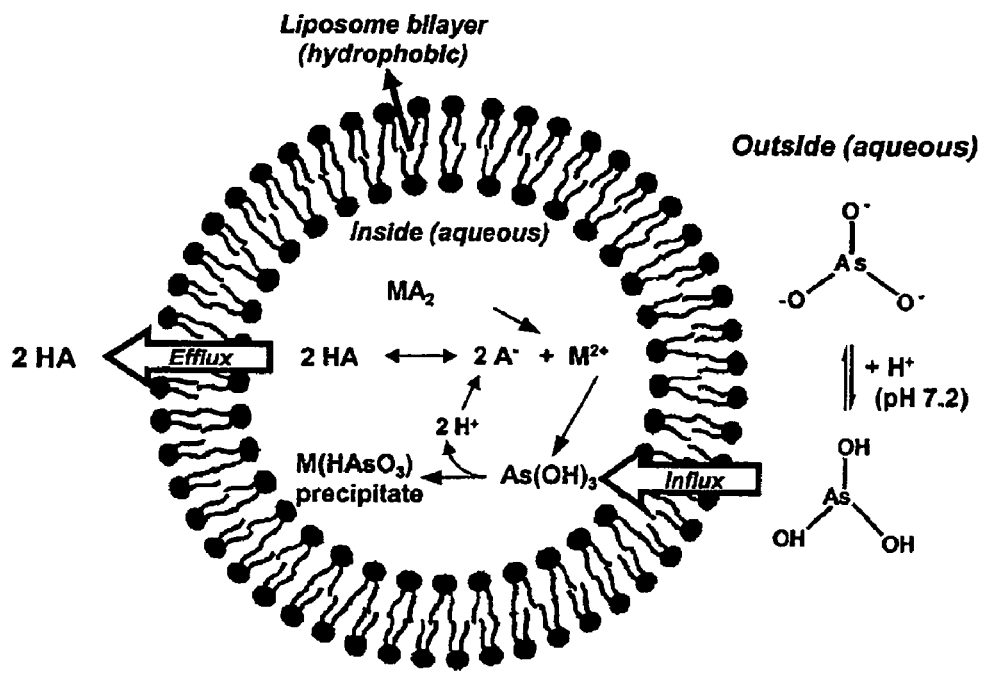
FIG. 2 shows a schematic representation of one exemplary method of the present invention for loading arsenic into a liposome in response to a transmembrane ion gradient.
Figure 4:
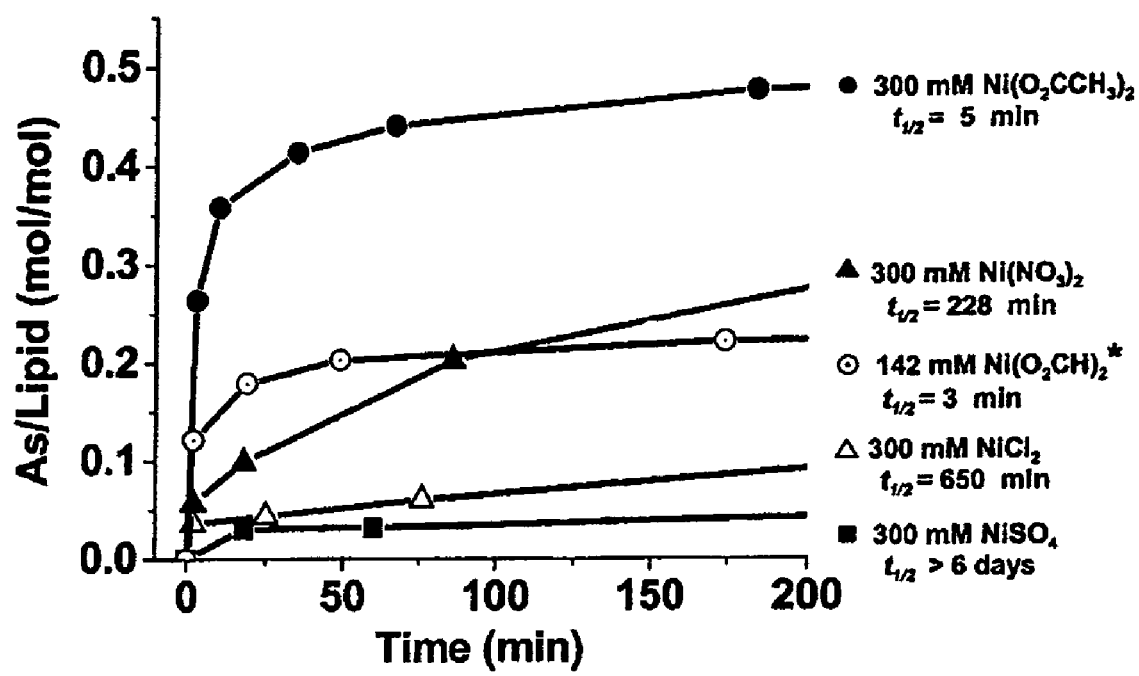
FIG. 4 shows arsenic loading efficiency dependent on the nature of anions of intraliposomal medium. The kinetics of arsenic loading into liposomes (DPPC/DOPG/Chol=65/5/30, wt %) with time using 300 mM $Ni(O_2CCH_3)_2$ (●), $Ni(NO_3)_2$ (▲), $NiCl_2$ (Δ), $NiSO_4$ (■) or 142 mM $Ni(O_2CH)_2$ (○) as intraliposomal medium at pH 6.8. Outer-buffer: 300 mM (●, ▲, Δ, ■) or 150 mM (○) NaCl, 20 mM HEPES and pH 7.2.
Figure 5:
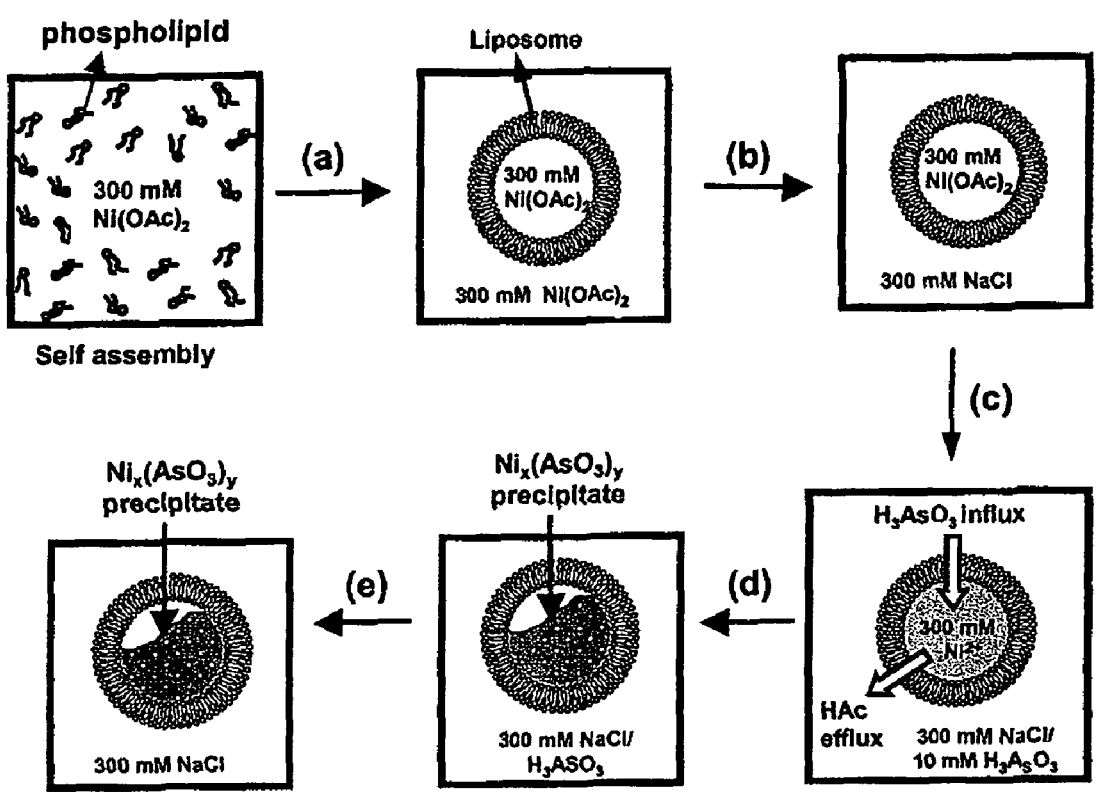
FIG. 5 shows the procedure of loading arsenic into liposomes by creating an inside to outside Ni(II) acetate (Ni(OAc)$_2$) gradient. (a) Dried lipids are hydrated in 300 mM Ni(OAc)$_2$ aqueous solution for 1.5 h at 50° C. to form 300 mM Ni(OAc)$_2$ encapsulated liposomes, which are thus downsized to 100 nm. (b) The external buffer of Ni(OAc)$_2$ is exchanged into 300 mM NaCl, 20 mM HEPES, pH 6.8 by using gel exclusion. (c) $As_2O_3$ or $NaAsO_2$ is added into liposomes at a certain As-to-Lipid molar ratio. (d) The influx of $H_3AsO_3$ into liposomes to form aggregation of $Ni_x(AsO_3)_y$, accompanied by the efflux of acetate acids (HAc) away from liposomes. (e) The excess of external $H_3AsO_3$ is removed by gel exclusion with the buffer of 300 mM NaCl, 20 mM HEPES and pH 4.0, followed by adjusting the pH of final liposome product back to 7.2.
Figure 6:
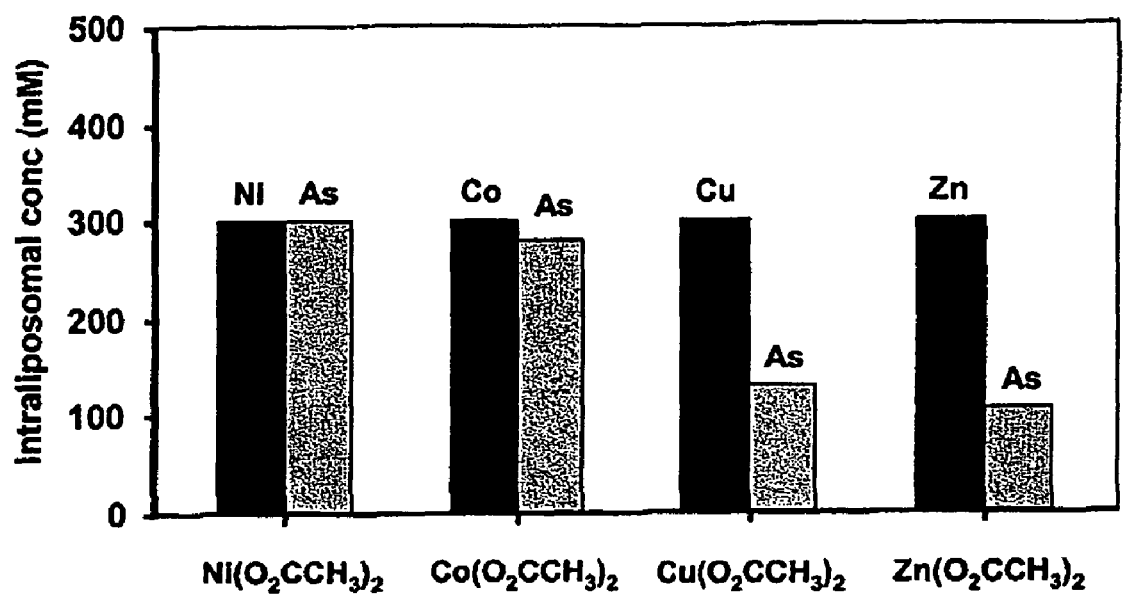
FIG. 6 shows a comparison of intraliposomal concentrations of $As^{3+}$ and $M^2$ ($Ni^{2+}$, $Co^{2+}$, $Cu^{2+}$ and $Zn^{2+}$) under similar conditions at equilibrium.
Figure 7:
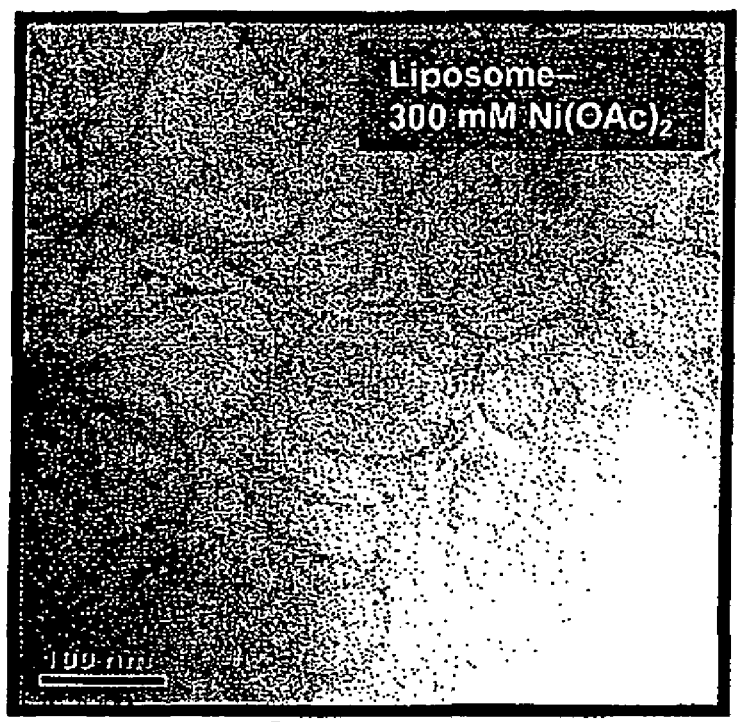
FIG. 7 shows transmission electron micrography (TEM) of liposomes (DPPC/DOPG/Chol: 65/5/30, wt %) before (A) or after (B) arsenic-loading using 300 mM Ni(OAc)$_2$ as intraliposomal medium.
Figure 7:
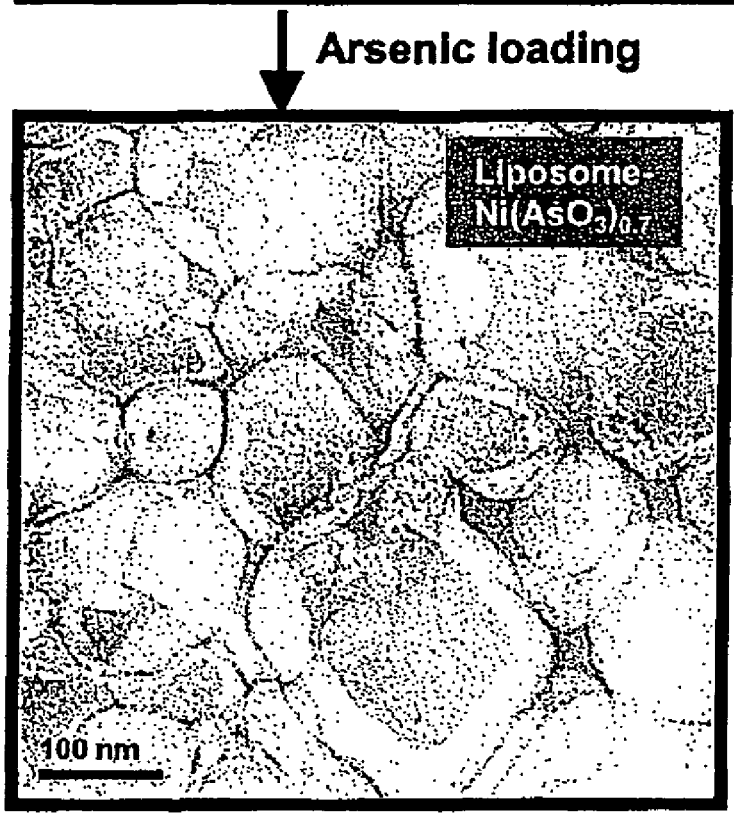

Based on the findings herein that arsenite could form both aqueous and hydrophobic insoluble complexes with transitional metal ions, such as $Ni^{2+}$, $Co^{2+}$, $Cu^{2+}$, $Zn^{2+}$, $Mn^{2+}$, $Fe^{2+}$, and $Pb^{2+}$ at neutral pH, and that such complexes are acid-sensitive and will re-dissolve when lowering pH values, an efficient system for encapsulating arsenic (III) drugs into liposomes has been created (see e.g., Example 3 and FIGS. 2, 4 and 5). An embodiment of this method involves first passively encapsulating a certain concentrated metal salt, such as 300 mM $Ni(O_2CCH_3)_2$, inside the liposomes, and removing the extraliposomal metal salt to create a gradient between the internal and external aqueous phase of liposomes (see the procedure in FIG. 5). This is followed by the addition of $NaAsO_2$ or $As_2O_3$ at pH 7.2, resulting in the active loading of arsenic(III) into liposomes with a half-life <5 min at 50° C. and with a final arsenic accumulation up to 300 mM within one 100-nm liposome vesicle (FIG. 6). This indicates that a single 100-nm liposome can carry greater than 90,000 arsenic molecules.

During a loading cycle, the external arsenite ions are protonated (at pH 7.2) to the neutral $As(OH)_3$ which diffuses across the lipid membrane to the internal liposome. By binding to $Ni^{2+}$ to form the insoluble nickel(II) arsenite complexes inside, such as $Ni(HAsO_3)$, $As(OH)_3$ releases two protons which bind to two acetate anions. The resulting acetic acids (HA) diffuse across the membrane to the external liposome in exchange for the influx of $As(OH)_3$, leading to significant accumulation of arsenic inside liposomes. Both the formation of insoluble nickel(II) arsenite complexes and the efflux of acetic acid are the driving forces for the arsenic uptake (FIG. 4). For this novel system, the $Ni^{2+}$ part can be any other transitional metal ions, such as $Co^{2+}$, $Cu^{2+}$, $Zn^{2+}$, $Mn^{2+}$, $Fe^{2+}$, and $Pb^{2+}$, which are able to form insoluble complexes with arsenite (under similar experimental conditions, using 300 mM sodium acetate as intraliposomal medium resulted in little arsenic uptake). The salt of sodium arsenite is water-soluble. The $Ac^-$ part can be any other anions ready to accept protons to form neutral compounds with lower molecular weight which can diffuse across the membrane rapidly, such as formate, lactate and hydroxyacetate (FIG. 4). The nature of the anion has significant influence on the efficiency of arsenic uptake as shown in Example 3 and FIG. 4. Under similar experimental conditions, the uptake rates are in the following order: 300 mM $Ni(O_2CCH_3)_2 \approx 142$ mM $Ni(O_2CH)_2 >> 300$ mM $Ni(NO_3)_2 > 300$ mM $NiCl_2 >> 300$ mM $NiSO_4$. There is little arsenic uptake in the case of 300 mM $NiSO_4$. Compared with the $pK_a$ values of acetic acid (4.75), formic acid (3.75), $HNO_3$ (−2), HCl (−7), and $H_2SO_4$ (−10), and considering the lower molecular weight and versatile properties for acetic acid, formic acid, nitric acid, and hydrochloric acid but not for sulfuric acid, arsenic loading efficiency appears to be facilitated by the ability of anions to accept protons for forming the neutral compounds which are ready to efflux from liposomes (FIG. 2).

The active loading of arsenic using other acetate salts of $M^{2+}$, such as $Co^{2+}$, $Cu^{2+}$, or $Zn^{2+}$ has shown similar behaviors to that of $Ni(O_2CCH_3)_2$ (Examples 4-6 and FIGS. 6, 10 and 11), and achieved the rapid equilibrium with half time <10 min. The final extent of arsenic uptake is somewhat less in the cases of $Cu^{2+}$ and $Zn^{2+}$ with the As-to-lipid molar ratio of 0.4 and 0.2, respectively, when compared with the 0.5 and 0.6 As-to-liposome molar ratios for $Ni^2$ and $Co^{2+}$ respectively (FIG. 6). Low uptake might be due to a less stable metal-arsenite complex, a different pH optimum for complex formation, and/or membrane permeability of the complex.

Figure 8:
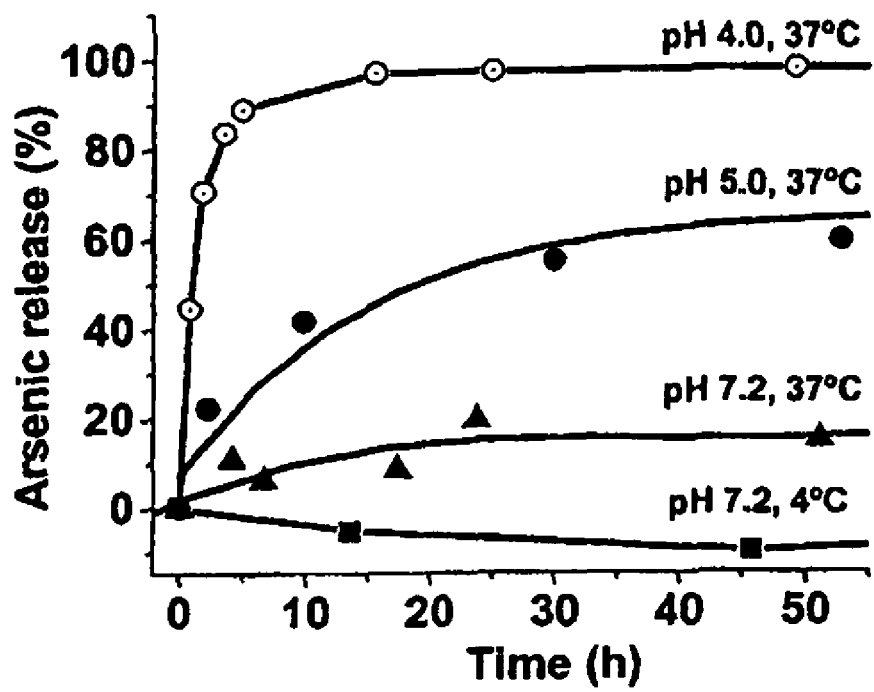
FIG. 8 shows temperature and pH triggered arsenic release from (A) Ni-arsenic-encapsulated and (B) Co-arsenic-encapsulated liposomes (DPPC/DOPG/Chol=65/5/30, wt %).
Figure 8:
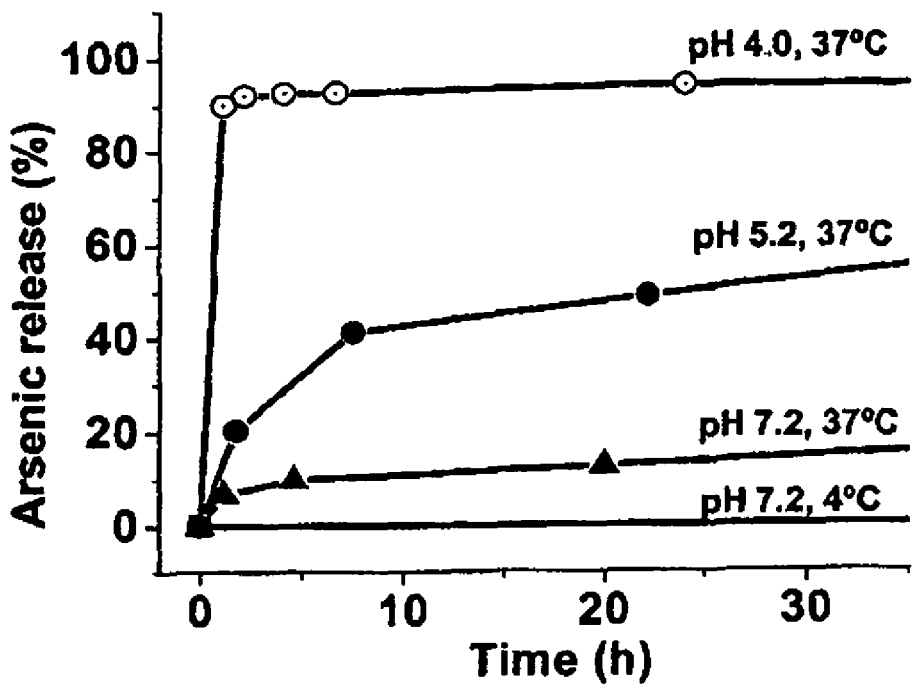

The novel liposomal $M_x(AsO_3)_y$ nano-particles show long shelf life (>6 months at 4° C. for Lip(Ni—As) and Lip(Co—As), Example 7 and FIG. 8). This meets the pharmaceutical requirements for clinical use. No "bedside" preparation of liposomal arsenic drugs is required immediately before patient treatment and the formulation is ready for injection. Due to the acid sensitivity of $M_x(AsO_3)_y$ complexes, the arsenic release is triggered by lowering pH values (Example 8 and FIG. 8). Lip(Co—As) particles are more acid-sensitive than Lip(Ni—As), which is consistent with the observation that the $Co_x(AsO_3)_y$ complex is almost completely dissolved when pH<5.5 while $Ni_x(AsO_3)_y$ is completely dissolved when pH<4.0. The accurate controlled release of arsenic can be realized by making use of different degree of acidic sensitivity of arsenite complexes with different transitional metals.

Figure 9:
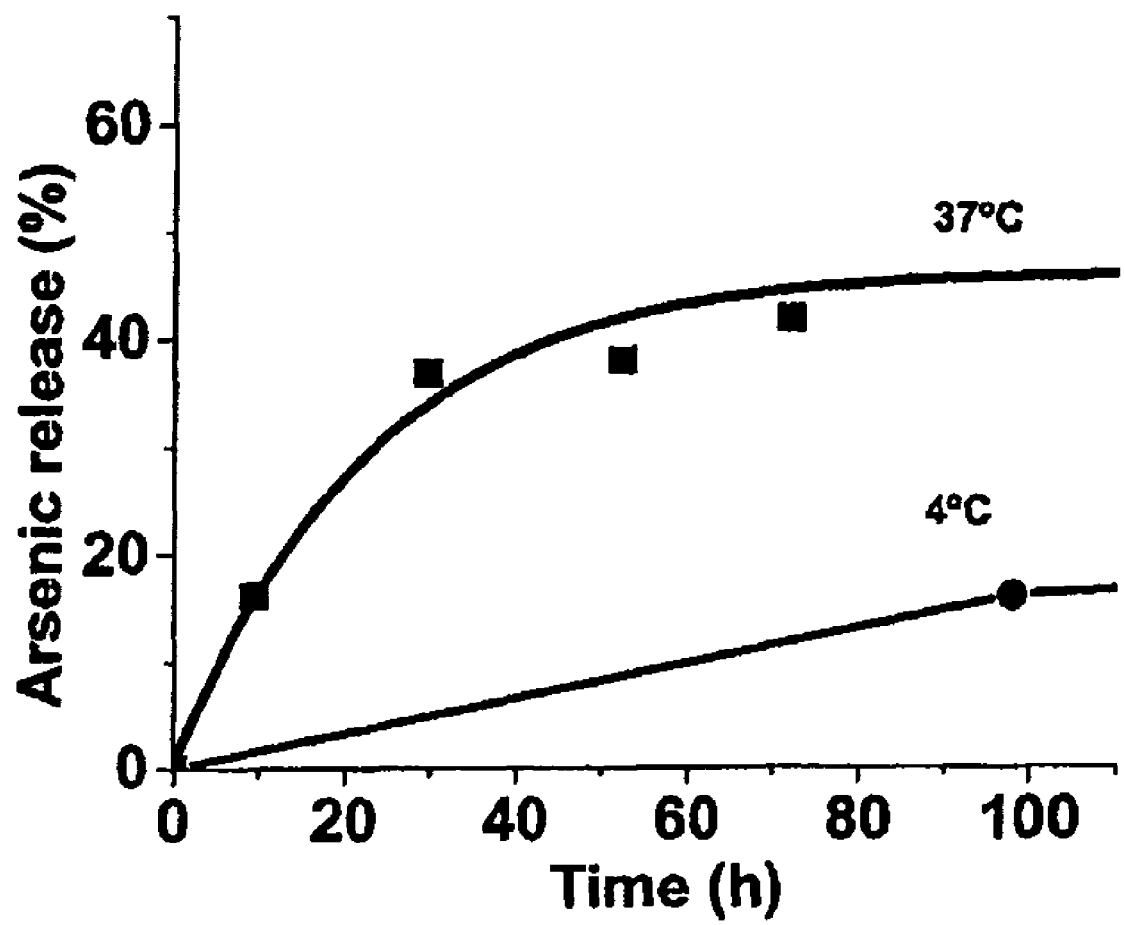
FIG. 9 shows arsenic release from Ni-arsenic-encapsulated liposomes (DOPC/DOPG/chol=65/5/30, wt %) at 4° C. (●) and 37° C. (■).

This drug loading system is also applicable to other types of liposomes. The more fluid lipids, such as dioleoylphosphatidylcholine (DOPC, with the gel-to-crystal transitional temperatures ($T_m$) of −20° C.) can be employed. Rapid and efficient uptake was achieved for liposomes with DOPC/dioleoylphosphatidylglycerol (DOPG)/Cholesterol (Chol) (65/5/30, wt %) as described in Example 9. FIG. 9 shows the stability for $Ni_x(AsO_3)_y$ inside liposomes at pH 7.2 with 16% release after 100 h storage at 4° C. The release was ten times faster when the temperature was raised to 37° C. Efficient loading was also achieved for the liposomes functionalized by PEG-2000 and Maleimide, with a 0.33 As-to-lipid molar ratio (Example 10). This loading system permits the preparation of arsenic-encapsulated liposomes with a broad spectrum of types, sizes, and composition, including sterically-stabilized liposomes, immunoliposomes, and sterically-stabilized immunolipsomes.

Figure 12:
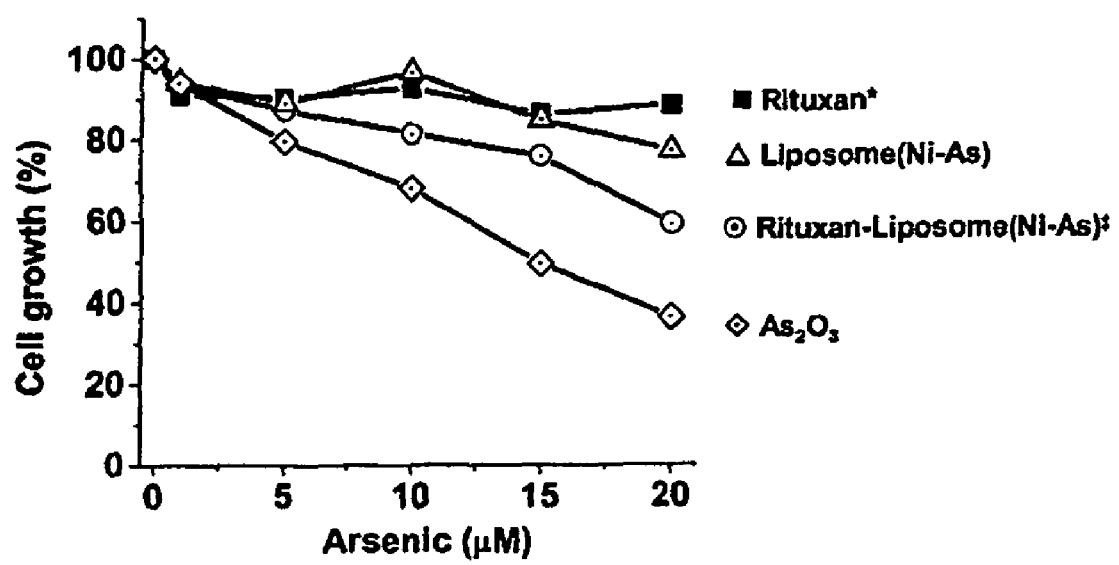
FIG. 12 shows the cytotoxicity effect of unencapsulated (◆) and encapsulated (Δ) and Rituxan-targeted encapsulated (○) arsenic drugs on SU-DHL-4 human lymphoma cells.

Monoclonal antibodies (mAb), such as anti-CD20 Rituxan, can be coupled to the Liposome(Ni—As) to provide the products of mAb-Lipsome(Ni—As) (Example 10). The cytotoxicities of Liposome(Ni—As) and Rituxan-Liposome (Ni—As) were tested on the human lymphoma cell line of SU-DHL-4 where CD20 antigens are expressed on the surface (Example 11). This was compared to the cytotoxicities of free $As_2O_3$ and Rituxan. It was found that when the cells were exposed to those drugs for a long period (three days at 37° C.) that most of encapsulated arsenic species were released from Liposome(Ni—As) ($IC_{50}$=1.92 µM) or Rituxan-Liposome (Ni—As) ($IC_{50}$=1.52 µM), and exhibited the killing ability as effective as the free $As_2O_3$ ($IC_{50}$=1.45 µM). When the cells were exposed to those drugs for a shorter time (20 min at 37° C.), the arsenic species were still sequestered inside liposomes, to be delivered to the tumor cell by the recognition of Rituxan to the CD20 on the cell surface. This is followed by release of arsenic for eradicating the tumor (FIG. 12).

II. Treatment of Disease

The liposome encapsulated drugs of the present invention find use in the treatment of a variety of disease states. Exemplary diseases include, but are not limited to cancer (e.g., leukemia), autoimmune disease (e.g., psoriasis and rheumatoid arthritis), tuberculosis, and syphilis.

A. Combination Therapy

In some embodiments, the compositions of the present invention are provided in combination with existing therapies. In other embodiments, two or more compounds of the present invention are provided in combination. In some embodiments, the compounds of the present invention are provided in combination with known cancer chemotherapy agents. The present invention is not limited to a particular chemotherapy agent.

Various classes of antineoplastic (e.g., anticancer) agents are contemplated for use in certain embodiments of the present invention. Anticancer agents suitable for use with the present invention include, but are not limited to, agents that induce apoptosis, agents that inhibit adenosine deaminase function, inhibit pyrimidine biosynthesis, inhibit purine ring biosynthesis, inhibit nucleotide interconversions, inhibit ribonucleotide reductase, inhibit thymidine monophosphate (TMP) synthesis, inhibit dihydrofolate reduction, inhibit DNA synthesis, form adducts with DNA, damage DNA, inhibit DNA repair, intercalate with DNA, deaminate asparagines, inhibit RNA synthesis, inhibit protein synthesis or stability, inhibit microtubule synthesis or function, and the like.

In some embodiments, exemplary anticancer agents suitable for use in compositions and methods of the present invention include, but are not limited to: 1) alkaloids, including microtubule inhibitors (e.g., vincristine, vinblastine, and vindesine, etc.), microtubule stabilizers (e.g., paclitaxel (TAXOL), and docetaxel, etc.), and chromatin function inhibitors, including topoisomerase inhibitors, such as epipodophyllotoxins (e.g., etoposide (VP-16), and teniposide (VM-26), etc.), and agents that target topoisomerase I (e.g., camptothecin and isirinotecan (CPT-11), etc.); 2) covalent DNA-binding agents (alkylating agents), including nitrogen mustards (e.g., mechlorethamine, chlorambucil, cyclophosphamide, ifosphamide, and busulfan (MYLERAN), etc.), nitrosoureas (e.g., carmustine, lomustine, and semustine, etc.), and other alkylating agents (e.g., dacarbazine, hydroxymethylmelamine, thiotepa, and mitomycin, etc.); 3) noncovalent DNA-binding agents (antitumor antibiotics), including nucleic acid inhibitors (e.g., dactinomycin (actinomycin D), etc.), anthracyclines (e.g., daunorubicin (daunomycin, and cerubidine), doxorubicin (adriamycin), and idarubicin (idamycin), etc.), anthracenediones (e.g., anthracycline analogues, such as mitoxantrone, etc.), bleomycins (BLENOXANE), etc., and plicamycin (mithramycin), etc.; 4) antimetabolites, including antifolates (e.g., methotrexate, FOLEX, and MEXATE, etc.), purine antimetabolites (e.g., 6-mercaptopurine (6-MP, PURINETHOL), 6-thioguanine (6-TG), azathioprine, acyclovir, ganciclovir, chlorodeoxyadenosine, 2-chlorodeoxyadenosine (CdA), and 2-deoxycoformycin (pentostatin), etc.), pyrimidine antagonists (e.g., fluoropyrimidines (e.g., 5-fluorouracil (ADRUCIL), 5-fluorodeoxyuridine (FdUrd) (floxuridine)) etc.), and cytosine arabinosides (e.g., CYTOSAR (ara-C) and fludarabine, etc.); 5) enzymes, including L-asparaginase, and hydroxyurea, etc.; 6) hormones, including glucocorticoids, antiestrogens (e.g., tamoxifen, etc.), nonsteroidal antiandrogens (e.g., flutamide, etc.), and aromatase inhibitors (e.g., anastrozole (ARIMIDEX), etc.); 7) platinum compounds (e.g., cisplatin and carboplatin, etc.); 8) monoclonal antibodies conjugated with anticancer drugs, toxins, and/or radionuclides, etc.; 9) biological response modifiers (e.g., interferons (e.g., IFN-α, etc.) and interleukins (e.g., IL-2, etc.), etc.); 10) adoptive immunotherapy; 11) hematopoietic growth factors; 12) agents that induce tumor cell differentiation (e.g., all-trans-retinoic acid, etc.); 13) gene therapy techniques; 14) antisense therapy techniques; 15) tumor vaccines; 16) therapies directed against tumor metastases (e.g., batimastat, etc.); 17) angiogenesis inhibitors; 18) proteosome inhibitors (e.g., VELCADE); 19) inhibitors of acetylation and/or methylation (e.g., HDAC inhibitors); 20) modulators of NF kappa B; 21) inhibitors of cell cycle regulation (e.g., CDK inhibitors); 22) modulators of p53 protein function; and 23) radiation.

Any oncolytic agent that is routinely used in a cancer therapy context finds use in the compositions and methods of the present invention. For example, the U.S. Food and Drug Administration maintains a formulary of oncolytic agents approved for use in the United States. International counterpart agencies to the U.S.F.D.A. maintain similar formularies. Table 1 provides a list of exemplary antineoplastic agents approved for use in the U.S. Those skilled in the art will appreciate that the "product labels" required on all U.S. approved chemotherapeutics describe approved indications, dosing information, toxicity data, and the like, for the exemplary agents.

TABLE 1

| | | |
|---|---|---|
| Aldesleukin (des-alanyl-1, serine-125 human interleukin-2) | Proleukin | Chiron Corp., Emeryville, CA |
| Alemtuzumab (IgG1κ anti CD52 antibody) | Campath | Millennium and ILEX Partners, LP, Cambridge, MA |
| Alitretinoin (9-cis-retinoic acid) | Panretin | Ligand Pharmaceuticals, Inc., San Diego CA |
| Allopurinol (1,5-dihydro-4H-pyrazolo[3,4-d]pyrimidin-4-one monosodium salt) | Zyloprim | GlaxoSmithKline, Research Triangle Park, NC |
| Altretamine (N,N,N',N',N'',N'',-hexamethyl-1,3,5-triazine-2,4,6-triamine) | Hexalen | US Bioscience, West Conshohocken, PA |
| Amifostine (ethanethiol, 2-[(3-aminopropyl)amino]-, dihydrogen phosphate (ester)) | Ethyol | US Bioscience |
| Anastrozole (1,3-Benzenediacetonitrile,a,a,a',a'-tetramethyl-5-(1H-1,2,4-triazol-1-ylmethyl)) | Arimidex | AstraZeneca Pharmaceuticals, LP, Wilmington, DE |
| Arsenic trioxide | Trisenox | Cell Therapeutic, Inc., Seattle, WA |

TABLE 1-continued

| | | |
|---|---|---|
| Asparaginase (L-asparagine amidohydrolase, type EC-2) | Elspar | Merck & Co., Inc., Whitehouse Station, NJ |
| BCG Live (lyophilized preparation of an attenuated strain of *Mycobacterium bovis* (Bacillus Calmette-Gukin [BCG], substrain Montreal) | TICE BCG | Organon Teknika, Corp., Durham, NC |
| bexarotene capsules (4-[1-(5,6,7,8-tetrahydro-3,5,5,8,8-pentamethyl-2-napthalenyl) ethenyl] benzoic acid) | Targretin | Ligand Pharmaceuticals |
| bexarotene gel | Targretin | Ligand Pharmaceuticals |
| Bleomycin (cytotoxic glycopeptide antibiotics produced by *Streptomyces verticillus*; bleomycin $A_2$ and bleomycin $B_2$) | Blenoxane | Bristol-Myers Squibb Co., NY, NY |
| Capecitabine (5'-deoxy-5-fluoro-N-[(pentyloxy)carbonyl]-cytidine) | Xeloda | Roche |
| Carboplatin (platinum, diammine [1,1-cyclobutanedicarboxylato(2-)-0,0']-,(SP-4-2)) | Paraplatin | Bristol-Myers Squibb |
| Carmustine (1,3-bis(2-chloroethyl)-1-nitrosourea) | BCNU, BiCNU | Bristol-Myers Squibb |
| Carmustine with Polifeprosan 20 Implant | Gliadel Wafer | Guilford Pharmaceuticals, Inc., Baltimore, MD |
| Celecoxib (as 4-[5-(4-methylphenyl)-3-(trifluoromethyl)-1H-pyrazol-1-yl] benzenesulfonamide) | Celebrex | Searle Pharmaceuticals, England |
| Chlorambucil (4-[bis(2chlorethyl)amino]benzenebutanoic acid) | Leukeran | GlaxoSmithKline |
| Cisplatin ($PtCl_2H_6N_2$) | Platinol | Bristol-Myers Squibb |
| Cladribine (2-chloro-2'-deoxy-b-D-adenosine) | Leustatin, 2-CdA | R. W. Johnson Pharmaceutical Research Institute, Raritan, NJ |
| Cyclophosphamide (2-[bis(2-chloroethyl)amino] tetrahydro-2H-13,2-oxazaphosphorine 2-oxide monohydrate) | Cytoxan, Neosar | Bristol-Myers Squibb |
| Cytarabine (1-b-D-Arabinofuranosylcytosine, $C_9H_{13}N_3O_5$) | Cytosar-U | Pharmacia & Upjohn Company |
| cytarabine liposomal | DepoCyt | Skye Pharmaceuticals, Inc., San Diego, CA |
| Dacarbazine (5-(3,3-dimethyl-1-triazeno)-imidazole-4-carboxamide (DTIC)) | DTIC-Dome | Bayer AG, Leverkusen, Germany |
| Dactinomycin, actinomycin D (actinomycin produced by *Streptomyces parvullus*, $C_{62}H_{86}N_{12}O_{16}$) | Cosmegen | Merck |
| Darbepoetin alfa (recombinant peptide) | Aranesp | Amgen, Inc., Thousand Oaks, CA |
| daunorubicin liposomal ((8S-cis)-8-acetyl-10-[(3-amino-2,3,6-trideoxy-á-L-lyxo-hexopyranosyl)oxy]-7,8,9,10-tetrahydro-6,8,11-trihydroxy-1-methoxy-5,12-naphthacenedione hydrochloride) | DanuoXome | Nexstar Pharmaceuticals, Inc., Boulder, CO |
| Daunorubicin HCl, daunomycin ((1S,3S)-3-Acetyl-1,2,3,4,6,11-hexahydro-3,5,12-trihydroxy-10-methoxy-6,11-dioxo-1-naphthacenyl 3-amino-2,3,6-trideoxy-(alpha)-L-lyxo-hexopyranoside hydrochloride) | Cerubidine | Wyeth Ayerst, Madison, NJ |
| Denileukin diftitox (recombinant peptide) | Ontak | Seragen, Inc., Hopkinton, MA |
| Dexrazoxane ((S)-4,4'-(1-methyl-1,2-ethanediyl)bis-2,6-piperazinedione) | Zinecard | Pharmacia & Upjohn Company |
| Docetaxel ((2R,3S)-N-carboxy-3-phenylisoserine, N-tert-butyl ester, 13-ester with 5b-20-epoxy-12a,4,7b,10b,13a-hexahydroxytax-11-en-9-one 4-acetate 2-benzoate, trihydrate) | Taxotere | Aventis Pharmaceuticals, Inc., Bridgewater, NJ |
| Doxorubicin HCl (8S,10S)-10-[(3-amino-2,3,6-trideoxy-a-L-lyxo-hexopyranosyl)oxy]-8-glycolyl-7,8,9,10-tetrahydro-6,8,11-trihydroxy-1-methoxy-5,12-naphthacenedione hydrochloride) | Adriamycin, Rubex | Pharmacia & Upjohn Company |

TABLE 1-continued

| | | |
|---|---|---|
| doxorubicin | Adriamycin PFS Intravenous injection | Pharmacia & Upjohn Company |
| doxorubicin liposomal | Doxil | Sequus Pharmaceuticals, Inc., Menlo park, CA |
| dromostanolone propionate (17b-Hydroxy-2a-methyl-5a-androstan-3-one propionate) | Dromostanolone | Eli Lilly & Company, Indianapolis, IN |
| dromostanolone propionate | Masterone injection | Syntex, Corp., Palo Alto, CA |
| Elliott's B Solution | Elliott's B Solution | Orphan Medical, Inc |
| Epirubicin ((8S-cis)-10-[(3-amino-2,3,6-trideoxy-a-L-arabino-hexopyranosyl)oxy]-7,8,9,10-tetrahydro-6,8,11-trihydroxy-8-(hydroxyacetyl)-1-methoxy-5,12-naphthacenedione hydrochloride) | Ellence | Pharmacia & Upjohn Company |
| Epoetin alfa (recombinant peptide) | Epogen | Amgen, Inc |
| Estramustine (estra-1,3,5(10)-triene-3,17-diol(17(beta))-, 3-[bis(2-chloroethyl)carbamate] 17-(dihydrogen phosphate), disodium salt, monohydrate, or estradiol 3-[bis(2-chloroethyl)carbamate] 17-(dihydrogen phosphate), disodium salt, monohydrate) | Emcyt | Pharmacia & Upjohn Company |
| Etoposide phosphate (4'-Demethylepipodophyllotoxin 9-[4,6-O-(R)-ethylidene-(beta)-D-glucopyranoside], 4'-(dihydrogen phosphate)) | Etopophos | Bristol-Myers Squibb |
| etoposide, VP-16 (4'-demethylepipodophyllotoxin 9-[4,6-0-(R)-ethylidene-(beta)-D-glucopyranoside]) | Vepesid | Bristol-Myers Squibb |
| Exemestane (6-methylenandrosta-1,4-diene-3,17-dione) | Aromasin | Pharmacia & Upjohn Company |
| Filgrastim (r-metHuG-CSF) | Neupogen | Amgen, Inc |
| floxuridine (intraarterial) (2'-deoxy-5-fluorouridine) | FUDR | Roche |
| Fludarabine (fluorinated nucleotide analog of the antiviral agent vidarabine, 9-b-D-arabinofuranosyladenine (ara-A)) | Fludara | Berlex Laboratories, Inc., Cedar Knolls, NJ |
| Fluorouracil, 5-FU (5-fluoro-2,4(1H,3H)-pyrimidinedione) | Adrucil | ICN Pharmaceuticals, Inc., Humacao, Puerto Rico |
| Fulvestrant (7-alpha-[9-(4,4,5,5,5-penta fluoropentylsulphinyl) nonyl]estra-1,3,5-(10)-triene-3,17-beta-diol) | Faslodex | IPR Pharmaceuticals, Guayama, Puerto Rico |
| Gemcitabine (2'-deoxy-2',2'-difluorocytidine monohydrochloride (b-isomer)) | Gemzar | Eli Lilly |
| Gemtuzumab Ozogamicin (anti-CD33 hP67.6) | Mylotarg | Wyeth Ayerst |
| Goserelin acetate (acetate salt of [D-Ser(But)$^6$,Azgly$^{10}$]LHRH; pyro-Glu-His-Trp-Ser-Tyr-D-Ser(But)-Leu-Arg-Pro-Azgly-NH2 acetate [$C_{59}H_{84}N_{18}O_{14}$•$(C_2H_4O_2)_x$ | Zoladex Implant | AstraZeneca Pharmaceuticals |
| Hydroxyurea | Hydrea | Bristol-Myers Squibb |
| Ibritumomab Tiuxetan (immunoconjugate resulting from a thiourea covalent bond between the monoclonal antibody Ibritumomab and the linker-chelator tiuxetan [N-[2-bis(carboxymethyl)amino]-3-(p-isothiocyanatophenyl)-propyl]-[N-[2-bis(carboxymethyl)amino]-2-(methyl)-ethyl]glycine) | Zevalin | Biogen IDEC, Inc., Cambridge MA |
| Idarubicin (5,12-Naphthacenedione, 9-acetyl-7-[(3-amino-2,3,6-trideoxy-(alpha)-L-lyxo-hexopyranosyl)oxy]-7,8,9,10-tetrahydro-6,9,11-trihydroxyhydrochloride, (7S-cis)) | Idamycin | Pharmacia & Upjohn Company |
| Ifosfamide (3-(2-chloroethyl)-2-[(2-chloroethyl)amino]tetrahydro-2H-1,3,2-oxazaphosphorine 2-oxide) | IFEX | Bristol-Myers Squibb |

TABLE 1-continued

| | | |
|---|---|---|
| Imatinib Mesilate<br>(4-[(4-Methyl-1-piperazinyl)methyl]-N-[4-methyl-<br>3-[[4-(3-pyridinyl)-2-pyrimidinyl]amino]-<br>phenyl]benzamide methanesulfonate) | Gleevec | Novartis AG, Basel,<br>Switzerland |
| Interferon alfa-2a<br>(recombinant peptide) | Roferon-A | Hoffmann-La Roche,<br>Inc., Nutley, NJ |
| Interferon alfa-2b<br>(recombinant peptide) | Intron A<br>(Lyophilized<br>Betaseron) | Schering AG, Berlin,<br>Germany |
| Irinotecan HCl<br>((4S)-4,11-diethyl-4-hydroxy-9-[(4-piperidinopiperidino)<br>carbonyloxy]-1H-pyrano[3',4':6,7]indolizino[1,2-<br>b]quinoline-3,14(4H,12H) dione hydrochloride trihydrate) | Camptosar | Pharmacia & Upjohn<br>Company |
| Letrozole<br>(4,4'-(1H-1,2,4-Triazol-1-ylmethylene)<br>dibenzonitrile) | Femara | Novartis |
| Leucovorin<br>(L-Glutamic acid, N[4[[(2amino-5-formyl-<br>1,4,5,6,7,8 hexahydro4oxo6-<br>pteridinyl)methyl]amino]benzoyl], calcium salt<br>(1:1)) | Wellcovorin,<br>Leucovorin | Immunex, Corp.,<br>Seattle, WA |
| Levamisole HCl<br>((−)-(S)-2,3,5,6-tetrahydro-6-phenylimidazo [2,1-<br>b]thiazole monohydrochloride $C_{11}H_{12}N_2S \cdot HCl$) | Ergamisol | Janssen Research<br>Foundation,<br>Titusville, NJ |
| Lomustine<br>(1-(2-chloro-ethyl)-3-cyclohexyl-1-nitrosourea) | CeeNU | Bristol-Myers Squibb |
| Meclorethamine, nitrogen mustard<br>(2-chloro-N-(2-chloroethyl)-N-methylethanamine<br>hydrochloride) | Mustargen | Merck |
| Megestrol acetate<br>17α(acetyloxy)-6-methylpregna-4,6-diene-<br>3,20-dione | Megace | Bristol-Myers Squibb |
| Melphalan, L-PAM<br>(4-[bis(2-chloroethyl) amino]-L-phenylalanine) | Alkeran | GlaxoSmithKline |
| Mercaptopurine, 6-MP<br>(1,7-dihydro-6H-purine-6-thione monohydrate) | Purinethol | GlaxoSmithKline |
| Mesna<br>(sodium 2-mercaptoethane sulfonate) | Mesnex | Asta Medica |
| Methotrexate<br>(N-[4-[[(2,4-diamino-6-<br>pteridmyl)methyl]methylamino]benzoyl]-L-<br>glutamic acid) | Methotrexate | Lederle Laboratories |
| Methoxsalen<br>(9-methoxy-7H-furo[3,2-g][1]-benzopyran-7-one) | Uvadex | Therakos, Inc., Way<br>Exton, Pa |
| Mitomycin C | Mutamycin | Bristol-Myers Squibb |
| mitomycin C | Mitozytrex | SuperGen, Inc.,<br>Dublin, CA |
| Mitotane<br>(1,1-dichloro-2-(o-chlorophenyl)-2-(p-<br>chlorophenyl) ethane) | Lysodren | Bristol-Myers Squibb |
| Mitoxantrone<br>(1,4-dihydroxy-5,8-bis[[2-[(2-<br>hydroxyethyl)amino]ethyl]amino]-9,10-<br>anthracenedione dihydrochloride) | Novantrone | Immunex<br>Corporation |
| Nandrolone phenpropionate | Durabolin-50 | Organon, Inc., West<br>Orange, NJ |
| Nofetumomab | Verluma | Boehringer Ingelheim<br>Pharma KG,<br>Germany |
| Oprelvekin<br>(IL-11) | Neumega | Genetics Institute,<br>Inc., Alexandria, VA |
| Oxaliplatin<br>(cis-[(1R,2R)-1,2-cyclohexanediamine-N,N']<br>[oxalato(2-)-O,O']platinum) | Eloxatin | Sanofi Synthelabo,<br>Inc., NY, NY |
| Paclitaxel<br>(5β,20-Epoxy-1,2a,4,7β,10β,13a-<br>hexahydroxytax-11-en-9-one 4,10-diacetate 2-<br>benzoate 13-ester with (2R, 3S)-N-benzoyl-3-<br>phenylisoserine) | TAXOL | Bristol-Myers Squibb |
| Pamidronate<br>(phosphonic acid (3-amino-1-hydroxypropylidene)<br>bis-, disodium salt, pentahydrate, (APD)) | Aredia | Novartis |
| Pegademase<br>((monomethoxypolyethylene glycol succinimidyl)<br>11-17-adenosine deaminase) | Adagen<br>(Pegademase<br>Bovine) | Enzon<br>Pharmaceuticals, Inc.,<br>Bridgewater, NJ |
| Pegaspargase<br>(monomethoxypolyethylene glycol succinimidyl<br>L-asparaginase) | Oncaspar | Enzon |
| Pegfilgrastim<br>(covalent conjugate of recombinant methionyl | Neulasta | Amgen, Inc |

TABLE 1-continued

| | | |
|---|---|---|
| human G-CSF (Filgrastim) and monomethoxypolyethylene glycol) | | |
| Pentostatin | Nipent | Parke-Davis Pharmaceutical Co., Rockville, MD |
| Pipobroman | Vercyte | Abbott Laboratories, Abbott Park, IL |
| Plicamycin, Mithramycin (antibiotic produced by *Streptomyces plicatus*) | Mithracin | Pfizer, Inc., NY, NY |
| Porfimer sodium | Photofrin | QLT Phototherapeutics, Inc., Vancouver, Canada |
| Procarbazine (N-isopropyl-μ-(2-methylhydrazino)-p-toluamide monohydrochloride) | Matulane | Sigma Tau Pharmaceuticals, Inc., Gaithersburg, MD |
| Quinacrine (6-chloro-9-(1-methyl-4-diethyl-amine) butylamino-2-methoxyacridine) | Atabrine | Abbott Labs |
| Rasburicase (recombinant peptide) | Elitek | Sanofi-Synthelabo, Inc., |
| Rituximab (recombinant anti-CD20 antibody) | Rituxan | Genentech, Inc., South San Francisco, CA |
| Sargramostim (recombinant peptide) | Prokine | Immunex Corp |
| Streptozocin (streptozocin 2-deoxy-2-[[(methylnitrosoamino)carbonyl]amino]-a(and b)-D-glucopyranose and 220 mg citric acid anhydrous) | Zanosar | Pharmacia & Upjohn Company |
| Talc ($Mg_3Si_4O_{10}(OH)_2$) | Sclerosol | Bryan, Corp., Woburn, MA |
| Tamoxifen ((Z)2-[4-(1,2-diphenyl-1-butenyl) phenoxy]-N,N-dimethylethanamine 2-hydroxy-1,2,3-propanetricarboxylate (1:1)) | Nolvadex | AstraZeneca Pharmaceuticals |
| Temozolomide (3,4-dihydro-3-methyl-4-oxoimidaz[5,1-d]-as-tetrazine-8-carboxamide) | Temodar | Schering |
| Teniposide, VM-26 (4'-demethylepipodophyllotoxin 9-[4,6-0-(R)-2-thenylidene-(beta)-D-glucopyranoside]) | Vumon | Bristol-Myers Squibb |
| Testolactone (13-hydroxy-3-oxo-13,17-secoandrosta-1,4-dien-17-oic acid [dgr]-lactone) | Teslac | Bristol-Myers Squibb |
| Thioguanine, 6-TG (2-amino-1,7-dihydro-6H-purine-6-thione) | Thioguanine | GlaxoSmithKline |
| Thiotepa (Aziridine, 1,1',1"-phosphinothioylidynetris-, or Tris (1-aziridinyl) phosphine sulfide) | Thioplex | Immunex Corporation |
| Topotecan HCl ((S)-10-[(dimethylamino) methyl]-4-ethyl-4,9-dihydroxy-1H-pyrano[3',4':6,7]indolizino [1,2-b] quinoline-3,14-(4H,12H)-dione monohydrochloride) | Hycamtin | GlaxoSmithKline |
| Toremifene (2-(p-[(Z)-4-chloro-1,2-diphenyl-1-butenyl]-phenoxy)-N,N-dimethylethylamine citrate (1:1)) | Fareston | Roberts Pharmaceutical Corp., Eatontown, NJ |
| Tositumomab, I 131 Tositumomab (recombinant murine immunotherapeutic monoclonal $IgG_{2a}$ lambda anti-CD20 antibody (I 131 is a radioimmunotherapeutic antibody)) | Bexxar | Corixa Corp., Seattle, WA |
| Trastuzumab (recombinant monoclonal $IgG_1$ kappa anti-HER2 antibody) | Herceptin | Genentech, Inc |
| Tretinoin, ATRA (all-trans retinoic acid) | Vesanoid | Roche |
| Uracil Mustard | Uracil Mustard Capsules | Roberts Labs |
| Valrubicin, N-trifluoroacetyladriamycin-14-valerate ((2S-cis)-2-[1,2,3,4,6,11-hexahydro-2,5,12-trihydroxy-7 methoxy-6,11-dioxo-[[4 2,3,6-trideoxy-3-[(trifluoroacetyl)-amino-α-L-lyxo-hexopyranosyl]oxyl]-2-naphthacenyl]-2-oxoethyl pentanoate) | Valstar | Anthra --> Medeva |
| Vinblastine, Leurocristine ($C_{46}H_{56}N_4O_{10} \cdot H_2SO_4$) | Velban | Eli Lilly |

TABLE 1-continued

| | | |
|---|---|---|
| Vincristine ($C_{46}H_{56}N_4O_{10} \cdot H_2SO_4$) | Oncovin | Eli Lilly |
| Vinorelbine (3',4'-didehydro-4'-deoxy-C'-norvincaleukoblastine [R-(R*,R*)-2,3-dihydroxybutanedioate (1:2)(salt)]) | Navelbine | GlaxoSmithKline |
| Zoledronate, Zoledronic acid ((1-Hydroxy-2-imidazol-1-yl-phosphonoethyl)phosphonic acid monohydrate) | Zometa | Novartis |

B. Pharmaceutical Compositions

The present invention further provides pharmaceutical compositions (e.g., comprising the liposome encapsulated compounds described above). The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary (e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration.

Pharmaceutical compositions and formulations for topical administration may include transdermal patches, ointments, lotions, creams, gels, drops, suppositories, sprays, liquids, etc.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

The compositions of the present invention may additionally contain other adjunct components conventionally found in pharmaceutical compositions. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Certain embodiments of the invention provide pharmaceutical compositions containing (a) one or more liposome encapsulated compounds of the present invention and (b) one or more other chemotherapeutic agents. Examples of such chemotherapeutic agents are described above. Anti-inflammatory drugs, including but not limited to nonsteroidal anti-inflammatory drugs and corticosteroids, and antiviral drugs, including but not limited to ribivirin, vidarabine, acyclovir and ganciclovir, may also be combined in compositions of the invention. Other chemotherapeutic agents are also within the scope of this invention. Two or more combined compounds may be used together or sequentially.

EXPERIMENTAL

The following examples are provided in order to demonstrate and further illustrate certain preferred embodiments and aspects of the present invention and are not to be construed as limiting the scope thereof.

Example 1

Materials and Methods

Materials

Lipids of Dipalmitoylphosphatidylcholine (DPPC), Dioleoylphosphatidylcholine (DOPC), Dioleoylphosphatidylglycerol (DOPG), Dipalmitoylphosphatidylethanolamine-poly(ethylene-glycol)(2000) (DPPE-PEG2000), Distearoylphosphatidylethanolamine-PEG2000-Maleimide (DSPE-PEG2000-Mal) were purchased from Avanti Polar Lipids (Alabaster, Ala., USA). Cholesterol (Chol), nickel(II) acetate, cobalt(II) acetate, copper(II) acetate, zinc(II) acetate, HEPES and NaCl were obtained from Sigma (Milwaukee, Wis., USA). Nickel(II) sulfate was from Mallinckrodt (Ky., USA). Sephadex G50 and Sepharose CL-4B were from Sigma. The chimeric murine/human anti-CD20 Rituxan was a generous gift from Dr. Steven Rosen (Robert H. Lurie Comprehensive Cancer Center, Northwestern University).

Methods

Preparation of Liposomes

All liposomes were made from either DPPC/DOPG/Chol (65:5:30, wt %) or DOPC/DOPG/Chol (65:5:30, wt %) and were prepared by extrusion methods (unless stated otherwise). Lipids, at the indicated ratios, were dissolved in chloroform. The chloroform was removed from the mixtures by gentle vacuum evaporation and subsequently, the lipids films were placed under a high vacuum for at least 4 h to remove any residual solvent. The dried samples were hydrated in the indicated solution to form multilamellar vesicles (MLVs), which were further subjected to ten freeze-and-thaw cycles (freezing in ethanol/dry-ice bath, −70° C. and thawing in water bath, 50° C.). The resulting MLVs was extruded 10 times through stacked polycarbonate filters of 0.4 and 0.1 or 0.8 µm pore size at 50-60° C. using a manual mini-extruder (Avanti Lipids, AL, USA). This gave a mean liposome size between 80 and 180 nm as determined by light scattering.

Preparation of Ion Gradients

The downsized liposomes prepared in the indicated solution were fractionated on Sephadex G-50 columns (1 mL sample volumes were placed on columns with at least a 20 mL column bed) equilibrated with various buffers. The buffers used for the external liposome included 150 mM or 300 mM NaCl and 20 mM HEPES, 300 mM sucrose and 20 mM HEPES at the indicated pH.

Methods for Quantification of Drug Loading

A concentrated solution of sodium arsenite (400 mM, pH 7.4) or arsenic trioxide (150 mM, pH 12.5) was added to the liposome dispersion (typically, 5 mM lipids) after the creation of an ion gradient. At various time points, aliquots were removed and passed through a Sephadex G-50 column to separate the unencapsulated drug from the encapsulated drug. The concentrations of lipids (P), encapsulated As and M (Ni, Co, Cu, or Zn) in the excluded fractions were determined by an Inductively Coupled Plasma Optical Emission Spectrometer (ICP-OES). The molar ratios of As/Lipid, M/lipid and As/M were calculated and used to assess loading efficiency.

Determination of Intraliposomal Concentration

Based on the kinetics of arsenic loading into 100-nm-liposomes using nickel(II) acetate (FIG. 11A), cobalt(II) acetate (FIG. 11B), copper(II) acetate, or zinc(II) acetate as intraliposomal medium, the metal ions ($M^{2+}$) inside liposomes are greatly retained with little leakage (<10%) within the loading period of 5 h at 50° C. The M-to-Lipid molar ratio of Lip(M-As) products can be assumed to correspond to the initial metal ion concentration. This, combined with the As-to-lipid molar ratio, is used to calculate the arsenic concentration inside the liposome. Typically, in the preparation of Lip(Ni—As) drug using 300 mM $Ni(O_2CCH_3)_2$ as intraliposomal medium, the Ni-to-Lipid molar ratio was found to be 0.5 at 2.5 h, which corresponds to the 300 mM $Ni^{2+}$ within one single liposome, and the As-to-Lipid molar ratio was 0.5, indicating there is 300 mM $As^{3+}$ within the same vesicle. A similar method was used to calculate the intraliposomal concentration of $As^{3+}$ and $M^{2+}$ for other Lip(M-As) drugs where 300 mM cobalt(II) acetate, copper(II) acetate or zinc(II) acetate was used as intraliposomal medium. The results are compared in FIG. 6.

Drug Release Assay

The in vitro arsenic release assay was carried out with liposome lipid concentrations of 0.9-2.6 mM. Samples were kept at 4° C. or 37° C. at the indicated pH. The extraliposomal buffer of 300 mM NaCl or 300 mM sucrose and 20 mM HEPES was used for pH 7.0-7.4; for pH 5.0-5.5, 30 mM MES was additionally added; and for pH 4.0, 40 mM acetic acid was additionally added. At the indicated time-points, aliquots were placed into a Sephadex G-50 column to remove arsenic drug, which leaked out from liposomes. The drug-to-lipid molar ratio in the excluded liposome fractions was determined as above. The drug release percentage (%) was calculated as $[(r_o-r_i)/r_o]\times 100\%$, $r_o$, initial As-to-Lipid molar ratio, $r_i$, the remained As-to-Lipid molar ratio at a specific time point.

Transmission Electron Microscopy

Liposome dispersions were imaged by transmission electron microscopy (TEM) at low dose. For negative stained TEM, the liposome samples were stained using 4% uranyl acetate and air-dried for 3 h before TEM loading. The TEM column vacumn is $1.0\times 10^{-6}$ Pa.

Thiolation of Rituxan

Rituxan was washed 4 times using a buffer of 150 mM NaCl, 20 mM HEPES, pH 7.1 (degassed under $N_2$) in Microcon-10. The concentration was determined by Bio-Rad Protein Assay. Purified Rituxan (10 mg/mL) was thus incubated with 2-iminothiolane in $O_2$-free buffer of 150 mM NaCl, 20 mM HEPES, pH 8.0 at a ratio of 20:1 mol/mol for 1 h at room temperature. This was followed by washing 4 times using 150 mM NaCl, 20 mM HEPES, pH 7.1 (degassed under $N_2$) in Amicon Ultra-4. The concentration of thiolated Rituxan was determined by Bio-Rad Protein Assay.

Determination of Rituxan/Liposome Ratio: CBQCA Assay

The amount of Rituxan coupled to the liposomes was determined by using a CBQCA (3-(4-carboxybenzoyl)quinoline-2-carboxalde-hyde) assay, where an increase in fluorescence is observed when CBQCA agent binds to a free amino group on the protein (You, W. W. et al. Anal. Biochem. (1997) 244: 277-282). Briefly, 5 mg of CBQCA was dissolved in 410 μL of Dimethylsulfoxide (DMSO). Aliquots (5-15 μL) of Rituxan-liposomal-arsenic were mixed with 10 μL of CBQCA solution and 5 μL of 20 mM KCN in the presence of 100 mM sodium borate buffer at pH 9.3 with a final volume of 150 μL. The reactions were carried out in a 96-well microplate. After 2 h incubation at room temperature with gentle shaking and protected from light, the relative fluorescence was determined on a Synergy HT Multi-detection Microplate Reader (EM 528 nm, EX 485 nm). Antibody concentration was determined from a standard curve of the known concentrations of free Rituxan with the presence of similar amount of lipids.

Cell Culture Experiments

The human lymphoma B cell line of SU-DHL-4 (CD20-positive) was obtained from the American Type Culture Collection (Rockville, Md., USA). Cells were cultured in RPMI 1640 (Invitrogen Corporation) supplemented with 10% fetal bovine serum, 2 mM glutamine, 100 units/mL penicillim, 100 μg/mL streptomycin, and 2.5 μg/mL fungizone. Cells were maintained at 37° C. in an incubator with 5% $CO_2$ and harvested in the exponential phase of growth.

Example 2

Arsenic Acids ($H_3AsO_3$) Pass Across Liposomal Membrane Too Rapidly for Drug Delivery Application The following experiment demonstrates why standard liposome loading methods will not work for arsenic drugs.

30 mg of dried lipid film of DPPC/DOPG/Chol (65/5/30, wt %) was hydrated in 0.9 mL of 150 mM sodium arsenite, or 75 mM $As_2O_3$ at pH 7.5 (pH was adjusted by concentrated HCl and 5 M NaOH) for 1.5 h at 50° C. For these two solutions, the major arsenic species is $H_3AsO_3$, (FIG. 1). This was subjected to 10 freeze-and-thaw cycles and then extruded 10 times through stacked polycarbonate filters of 0.4 and 0.1 μm pore size at 50° C. After removal of the extra liposomal arsenic species with Sephadex G-50 using a buffer of 150 mM NaCl, 20 mM HEPES, pH 7.0, the dispersion of sodium arsenite or $As_2O_3$-encapsulated liposomes (2.0 mL) was kept on a 4° C. ice bath. At various time points, 125-200 μL aliquots were passed through Sephadex G-50 to remove arsenic species that leaked out from liposomes. At each time point, the extent of encapsulated drug was determined as As/Lipid molar ratio as described in Example 1. The arsenic release % against the time is plotted in FIG. 3, showing that the encapsulated arsenic species very readily release both in the cases of sodium arsenite and arsenic trioxide, with half-times <50 min at 4° C. and >90% leakage after 24 h. This half-life is too short for appropriate pharmacokenetics and seriously limits the shelf-life of drugs.

Example 3

Arsenic Loading Using Metal Ion Gradients 15-20 mg of dried lipid film of DPPC/DOPG/Chol (65/5/30, wt %) was hydrated in 0.5-0.6 mL of 300 mM $Ni(O_2CCH_3)_2$, $Ni(NO_3)_2$, $NiCl_2$ and $NiSO_4$ and 142 mM $Ni(O_2CH)_2$ at pH 6.8 (the pH of Ni(II) salts were adjusted by concentrated HCl or NaOH solution when necessary) for 1.5 h at 50° C., respectively. This was subjected to 10 freeze-and-thaw cycles and then extruded 10 times through stacked polycarbonate filters of 0.4 μm and 0.1 μm pore size at 50-60° C. After removal of extraliposomal nickel salts with Sephadex G-50 using a buffer of 300 mM (150 mM for the case of $Ni(O_2CH)_2$) NaCl and 20 mM HEPES, pH 6.8, 60-90 μL of 150 mM arsenic trioxide was added to these nickel-encapsulated liposomes (1.5-1.8 mL) at a lipid concentration of 5 mM, and the pH of mixture was adjusted to 7.2. This was incubated at 50° C. with frequent vortexing. At various time points, 80-130 μL aliquots were passed through Sephadex G-50 with the same buffer at pH 4.0 to remove unencapsulated arsenic and nickel species. The extent of encapsulated drug at each time point was determined as As/Lipid molar ratio as described in Example 1. FIG. 4 shows the kinetics of arsenic loading into liposomes using various salts of nickel (II) as an intraliposomal medium.

For the cases of 300 mM $Ni(O_2CCH_3)_2$ and 142 mM $Ni(O_2CH)_2$, efficient arsenic loading with As-to-lipid molar ratios of 0.5 and 0.22, respectively, was achieved after 60 min with a half time of <5 min. For 300 mM $NiSO_4$, there was little uptake of arsenic even after one week. For 300 mM $NiCl_2$, the arsenic uptake was very slow with the half time of 650 min and achieved a final As-to-lipid ratio of 0.35 after 24 h; for 300 mM $Ni(NO_3)_2$, the uptake appeared to be three times faster than that of $NiCl_2$ with a half-time of 228 min, and achieved a final As-to-lipid molar ratio of 0.5 after 10 h.

Example 4

Figure 10:
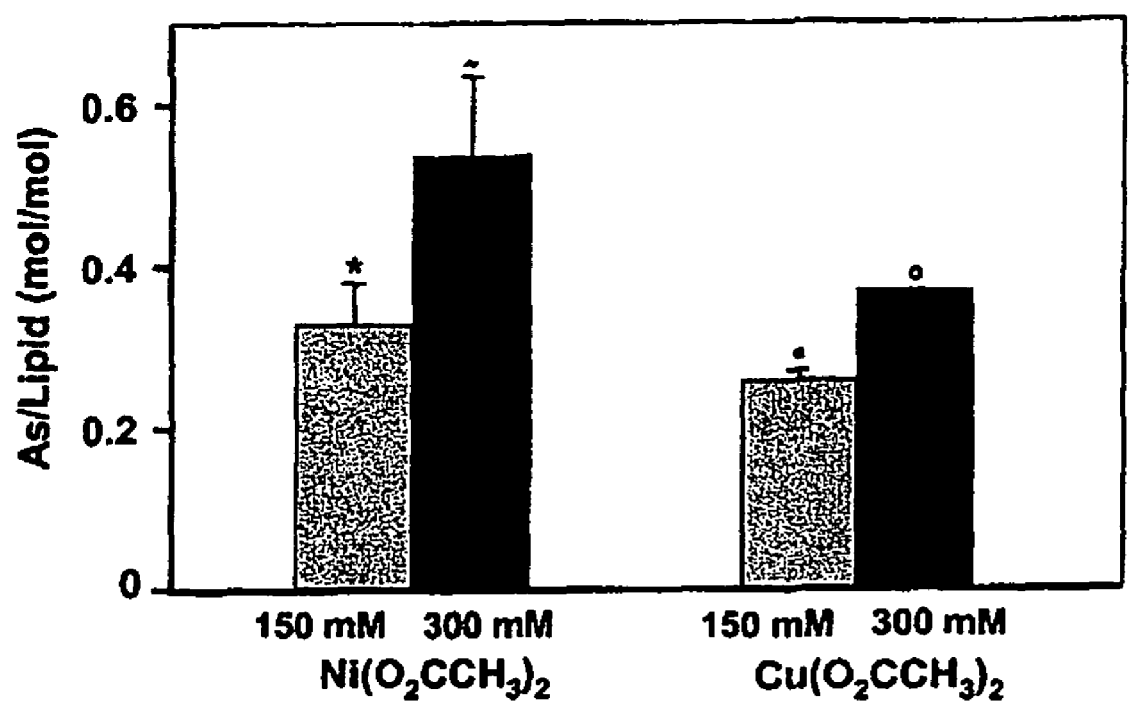
FIG. 10 shows the extent of arsenic loading into liposomes (DPPC/DOPG/chol=65/5/30, wt %) increased with concentrations of intraliposomal $Ni(O_2CCH_3)_2$ or $Cu(O_2CCH_3)_2$ solutions.
Figure 11:
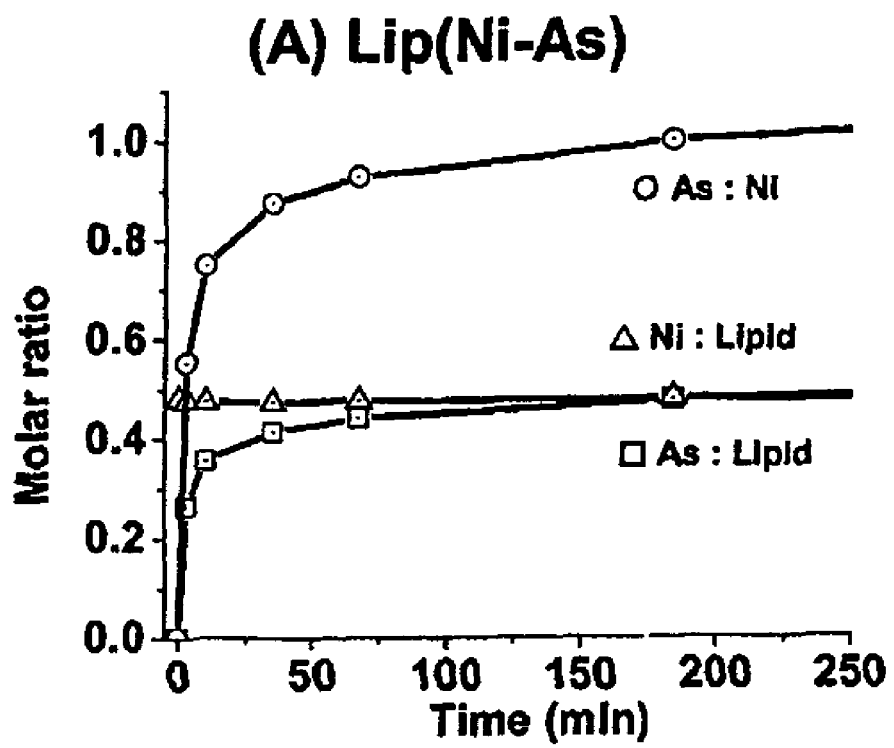
FIG. 11 shows the kinetics of arsenic loading into liposomes (DPPC/DOPG/Chol=65/5/30, wt %) using 300 mM (A) $Ni(O_2CCH_3)_2$, pH 6.8, or (B) $Co(O_2CCH3)_2$, pH 7.2, as intraliposomal medium, with an initial As-to-Lipid molar ratio of 2.0 at 50° C.
Figure 11:
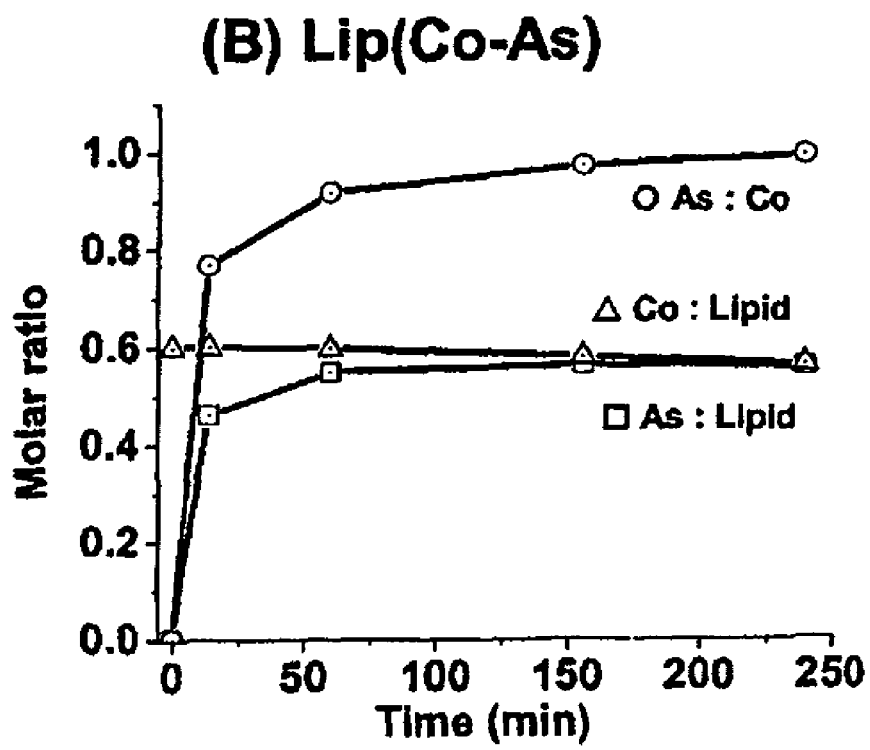

Arsenic Loading Using Copper Ion Gradients 30 mg of dried lipid film of DPPC/DOPG/Chol (65/5/30, wt %) was hydrated in 0.9 mL of 150 mM $Cu(O_2CCH_3)_2$, pH 5.4 for 1.5 h at 50° C. This was subjected to 10 freeze-and-thaw cycles and then extruded 10 times through stacked polycarbonate filters of 0.4 μm and 0.1 μm pore size at 60° C. After removal of extraliposomal $Cu(O_2CCH_3)_2$ with Sephadex G-50 using a buffer of 150 mM NaCl, 20 mM HEPES, pH 5.1, 100 μL of 150 mM arsenic trioxide was added to these copper-encapsulated liposomes (2.0 mL) at a lipid concentration of 5 mM and the mixture was adjusted to pH 6.0. This was incubated at 50° C. with frequent vortexing. At various time points, 200 μL aliquots were passed through Sephadex G-50 with the same buffer at pH 3.8 to remove unencapsulated arsenic and copper species. The extent of encapsulated drug at each time point was determined as As/Lipid molar ratio as described in Example 1. The loading was complete after 1 h with a half-life of 8 min. The final As/Lipid molar ratio is 0.24. A similar experiment was carried out using 300 mM $Cu(O_2CCH_3)_2$ as intraliposomal medium, which gave the final As/Lipid molar ratio of 0.37 (FIG. 10).

Example 5

Arsenic Loading Using Cobalt Ion Gradients 30 mg of dried lipid film of DPPC/DOPG/Chol (65/5/30, wt %) was hydrated in 0.9 mL of 300 mM $Co(O_2CCH_3)_2$, pH 7.2 for 1.5 h at 50° C. This was subjected to 10 freeze-and-thaw cycles and then extruded 10 times through stacked polycarbonate filters of 0.4 μm and 0.1 μm pore size at 60° C. After removal of the extraliposomal $Co(O_2CCH_3)_2$ with Sephadex G-50 using a buffer of 300 mM NaCl, 20 mM HEPES, pH 6.9, 100 μL of 150 mM arsenic trioxide was added to these cobalt-encapsulated liposomes (1.8 mL) and the mixture was adjusted to pH 7.3. This was incubated at 50° C. with frequent vortexing. At various time points, 200 μL aliquots were passed through Sephadex G-50 with the same buffer at pH 5.4 to remove encapsulated arsenic and cobalt species. The extent of encapsulated drug at each time point was determined as As/Lipid molar ratio as described in Example 1. FIG. 11(B) shows the kinetics of arsenic loading into liposomes using 300 mM $Co(O_2CCH_3)_2$ as intraliposomal medium. The loading was completed after 1 h with the half-life of 8 min and the final As/Lipid molar ratio is 0.6.

Example 6

Arsenic Loading Using Zinc Ion Gradients 60 mg of dried lipid film of DPPC/DOPG/Chol (65/5/30, wt %) was hydrated in 1.6 mL of 300 mM zinc acetate, pH 6.1, for 1.5 h at 50° C. This was subjected to 10 freeze-and-thaw cycles and then extruded 10 times through stacked polycarbonate filters of 0.1 μm pore size at 60° C. After removal of the extraliposomal zinc acetate with Sephadex G-50 using a buffer of 300 mM sucrose, 20 mM HEPES, pH 5.9, 107 μL of 400 mM $NaAsO_2$ was added to these zinc-encapsulated liposomes (2.9 mL) and the mixture was adjusted to pH 6.4. This was incubated at 50° C. with frequent vortexing. 0.2 mL of aliquot at a time of 1 h, and 0.5 mL at 2 h and 4 h were withdrawn and passed through Sephadex G-50 with the same buffer at pH 4.0 to remove unencapsulated arsenic and zinc species. The loading equilibrium was achieved after 1 h. The extent of encapsulated drug was determined as As/Lipid molar ratios of 0.23. A similar experiment was carried out with the addition of an amount of arsenic trioxide into the zinc acetate encapsulated liposomes, which gave the final As/Lipid molar ratios of 0.21.

Example 7

Stability of Liposome Components

The sample of As—Ni-encapsulated liposomes with a 0.5 As-to-lipid molar ratio and 2.6 mM lipids in the outer buffer of 300 mM sucrose, 20 mM HEPES, pH 7.2 was kept at 4° C. At various time points, 150 μL aliquots were passed through Sephadex G-50 with the same buffer at pH 4.0 to remove the extraliposomal arsenic. The drug release % at each time point was determined as described in Example 1. FIG. 8A shows there is little leakage of arsenic (<5%) after six months of storage at 4° C. at pH 7.2.

The sample of As—Co-encapsulated liposomes with a 0.5 Co-to-lipid molar ratio and 0.9 mM lipids in the outer buffer of 300 mM NaCl, 20 mM HEPES, pH 7.2 was kept at 4° C. At various time points, 330 μL aliquots were passed through Sephadex G-50 with the same buffer at pH 4.0 to remove the extraliposomal arsenic. The drug release % at each time point was determined as described in Example 1. FIG. 8B shows there was little leakage of arsenic (<5%) after six months of storage at 4° C. at pH 7.2.

Example 8

Arsenic Release Triggered by Temperature and Intracellular pH Gradients

The samples of As—Ni-encapsulated- or Co—As-encapsulated-liposomes with a 0.6 As-to-lipid ratio and 1.0-1.7 mM lipids were kept at 37° C. in a buffer of 300 mM NaCl, 20 mM HEPES at pH 7.2, pH 5.0 (+30 mM MES) or pH 4.0 (+40 mM acetic acid). At various time points, 200-390 μL aliquots were passed through Sephadex G-50 with the same buffer at pH 4.0 to remove the extraliposomal arsenic. The drug release % at each time point was determined as described in Example 1 (FIG. 8).

FIG. 8A shows that for Lip(Ni—As) liposomes at pH 7.2, there was 15% release after 24 h incubation at 37° C., compared with little release at 4° C. When the pH was decreased to 5.0, 55% arsenic was released after 24 h at 37° C.; when the pH was further decreased to 4.0, the release was 24× faster than that at pH 5.0, with 50% release after 1 h and over 95% release after 13 h. FIG. 8B shows that for Lip(Co—As) liposomes at pH 7.2, there was 14% release after 24 h incubation at 37° C., compared with little release at 4° C.; when pH was decreased to 5.2, 50% arsenic was released after 24 h at 37° C.; when pH was further decreased to 4.0, the release was 40× faster than that at pH 5.2, with 50% release after 0.6 h and over 90% release after 1.1 h.

Example 9

Arsenic Loading into Liposomes with Fluid Lipids 60 mg of dried lipid film of DOPC/DOPG/Chol (65/5/30, wt %) was hydrated in 1.6 mL of 300 mM $Ni(O_2CCH_3)_2$, pH 6.9 for 1 h at 37° C. This was subjected to 10 freeze-and-thaw cycles and then extruded 10 times through stacked polycarbonate filters of 0.4 μm and 0.08 μm pore size at 40° C. After removal of the extraliposomal $Ni(O_2CCH_3)_2$ with Sephadex G-50 using a buffer of 300 mM NaCl, 20 mM HEPES, pH 6.9, 210 μL of 150 mM arsenic trioxide was added to these nickel-encapsulated liposomes (5 mL) and the mixture was adjusted to pH 7.2. This was incubated at 37° C. with frequent vortexing. A 0.4 mL of aliquot at a time of 1 h, 3.8 mL at 2.5 h and 0.5 mL at 4 h were withdrawn and passed through Sephadex G-50 with the same buffer at pH 4.0 to remove unencapsulated arsenic and nickel species. The extent of encapsulated drug at each time point was determined as As/Lipid molar ratio as described in Example 1 with an As-to-Lipid ratio of 0.86 (1 h), 1.0 (2.5 h), and 1.0 (4 h). The results indicate the loading was almost complete after 1 h at 37° C.

Stability and Release Assay. The samples of As—Ni-encapsulated liposomes of DOPC/DOPG/Chol (65/5/30, wt %) with a 1.0 As-to-lipid molar ratio and 1.0 mM lipids in the outer buffer of 300 mM NaCl, 20 mM HEPES, pH 7.2 were kept in at 4° C. and 37° C. At various time points, 300-330 μL aliquots were passed through Sephadex G-50 with the same buffer at pH 4.0 to remove the extraliposomal arsenic. The drug release % at each time point was determined and plotted against time (FIG. 9). There is 16% release of arsenic from liposome after 100 h of storage at 4° C. and pH 7.2. The release was ten times faster when stored at 37° C. where 16% arsenic was released after only 9 h.

Preparation of Immunoliposomal Arsenic PEGlated and Maleimided Liposome(Ni—As).

35.4 mg of a dried lipid film of DPPC/DPPE-PEG2000/DSPE-PEG2000-Mal/Chol (66.4/2.6/1/30, mol %) was hydrated in 1.1 mL of 300 mM $Ni(O_2CCH_3)_2$, pH 6.9 for 1.5 h at 50° C. This was subjected to 10 freeze-and-thaw cycles and then extruded 10 times through stacked polycarbonate filters of 0.4 μm and 0.08 μm pore size at 60° C. After removal of extraliposomal $Ni(O_2CCH_3)_2$ with Sephadex G-50 using a buffer of 300 mM NaCl, 20 mM HEPES, pH 6.9, 130 μL of 150 mM arsenic trioxide was added to the liposome dispersion (2.4 mL) and the pH of mixture was adjusted to 7.3. This was incubated at 50° C. for 2.5 h with frequent vortexing. The mixture was adjusted to pH 4.0, and allowed to passed through Sephadex G-50 with the same buffer at pH 4.0 to remove unencapsulated arsenic and nickel species. The pH values of the excluded fractions were adjusted back to 7.2. The extent of encapsulated drug was determined as the As-to-Lipid molar ratio of 0.33, as described in Example 1.

Rituxan-Liposome(Ni—As).

To the PEGlated and Maleimided Liposomal(Ni—As) complex (2.7 mL), thiolated Rituxan (freshly prepared, see Example 1) was added at a molar ratio of 1:223 (Rituxan/Lipid). This was stirred overnight at room temperature in an $O_2$-free environment. The mixture was then passed through Sepharose CL-4B using a buffer of 300 mM NaCl, 20 mM HEPES, pH 7.1 to separate the unconjugated Rituxan. The density of Rituxan coupled to liposomes was determined as 30.1 μg Rituxan/μmol Lipid, as described in Example 1. This is conversed to 19 Rituxan molecules per liposome, based on the assumption that there are approximately $7.7 \times 10^{12}$ liposomes at 100 nm scale per μmol of lipids (Hansen, C. B., et al. Biochim. Biophys. Acta (1995) 1239: 133-144). The As-to-Lipid molar ratio is 0.24.

Example 10

The aggregation of arsenic drugs inside liposomes can be reversed under specific conditions. Thus, the active drug has the potential to be released from liposome-arsenic conjugates once they are delivered to tumor cells. The following example demonstrates that targeted liposomal arsenic drugs are as effective as the parent drug for killing tumor cells but with lower toxicity towards healthy cells, through lipid coating and antibody delivery.

Cytotoxicity Assays

The in vitro cytotoxicity of free $As_2O_3$, free Rituxan, Liposome(Ni—As), and Rituxan-Liposome(Ni—As) on human lymphoma cell line SU-DHL-4 was determined using a MTS (3-(4,5-dimethylthiazol-2-yl)-5-(3-carboxymethoxyphenyl)-2-(4-sulfophenyl)-2H-tetrazolium) assay as described previously (Lopes de Menezes, D. E. et al. Biochim. Biophys. Acta (2000) 1466: 205-220). Cells (25,000 cells/mL) were treated with various drugs and plated in 96-well plates. After incubation for 72 h at 37° C., the MTS solution (20 μL/well) was added to each well and the plates were further incubated for 4 h at 37° C. before the absorbance readings at 490 nm. The $IC_{50}$ values (the drug concentration required for 50% inhibition of cell growth) were determined based on simple fit curves of cell growth % against drug concentration (arsenic level): $As_2O_3$, 1.45 μM; Liposome(Ni—As), 1.92 μM; Rituxan-Liposome(Ni—As), 1.52 μM. This indicates that after a three-day exposure at 37° C., the encapsulated arsenic had similar cell killing effects as that of free $As_2O_3$, through releasing from Liposome(Ni—As), or from Rituxan-Liposome(Ni—As). A similar amount of free Rituxan to that of Rituxan-Liposome(Ni—As) was used to treat cells for comparison. It was found that there was no significant influence of free Rituxan (<3000 ng/mL) on cell growth.

In a parallel experiment, SU-DHL-4 cells (100,000 cells/mL) were treated with various drugs and plated in 96-well plates. After incubation at 37° C. for 20 min, cells were washed twice using 200 μL/well of PBS and refilled with 100 μL/well of fresh medium and incubated for an additional 71.6 h. The MTS solution (20 μL/well) was added to each well and the plates were further incubated for 4 h at 37° C. before taking the absorbance readings at 490 nm. The inhibited growth of cells in the presence of various drugs are displayed in FIG. 12, showing there was no significant effect from Liposome(Ni—As) and free Rituxan when compared with that of the free $As_2O_3$ and the Rituxan-Liposome(Ni—As). The Rituxan conjugation improved the inhibition effect of Liposome(Ni—As). This indicates that within the first 20 min exposure to free $As_2O_3$ at 37° C., the cells might already accumulate a significant amount of arsenic since the $H_3AsO_3$ has high permeability through the membrane. When sheltered by the liposome bilayer, the possibility of arsenic reaching cells is greatly reduced, indicating that lipid coating could prevent the killing of healthy cells. Through conjugating to the mAb of Rituxan, liposome(Ni—As) could be delivered to cells by Rituxan binding to the CD20 antigen on the cell surface. This was followed by the release of arsenic from liposomes, leading to inhibition of cell growth.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the art are intended to be within the scope of the following claims.

We claim:

1. A composition comprising a stable therapeutic preparation of liposome, wherein said liposome encapsulates a metal and arsenic trioxide, wherein said metal is Ni, and wherein said liposome comprises a targeting ligand, wherein said targeting ligand comprises folate.

2. The composition of claim 1, wherein said liposome is stable under physiological conditions.

3. The composition of claim 1, wherein said liposome further encapsulates an amphiphilic drug different from said arsenic trioxide.

4. The composition of claim 1, wherein said stable therapeutic preparation has a shelf-life of greater than one month.

5. A method for making a pharmaceutical preparation comprising a liposome, comprising,
   a) providing a liposome, wherein said liposome comprises folate;
   b) combining said liposome with a metal ion under conditions such that said metal ion is encapsulated in said liposome, wherein said metal ion is Ni; and
   c) contacting said liposome comprising said encapsulated metal ion with arsenic trioxide under conditions such that said arsenic trioxide is encapsulated in said liposome.

6. The method of claim 5, wherein said arsenic trioxide is released from said liposome at a condition selected from the group consisting of low pH, temperature change or contact with a second liposome comprising a fluid liposome with a lower gel to crystal transition temperature than said liposome.

7. A pharmaceutical preparation made by the method comprising:
   a) providing a liposome, wherein said liposome comprises folate;
   b) combining said liposome with a metal ion under conditions such that said metal ion is encapsulated in said liposome, wherein said metal ion is Ni; and
   c) contacting said liposome comprising said encapsulated metal ion with arsenic trioxide under conditions such that said arsenic trioxide is encapsulated in said liposome.

8. A method of treating breast cancer, comprising administering a composition to a subject with breast cancer, wherein said composition comprises a stable therapeutic preparation of liposome, wherein said liposome encapsulates Ni and arsenic trioxide.

* * * * *

UNITED STATES PATENT AND TRADEMARK OFFICE
CERTIFICATE OF CORRECTION

| | | |
|---|---|---|
| PATENT NO. | : 8,246,983 B2 | Page 1 of 1 |
| APPLICATION NO. | : 11/515711 | |
| DATED | : August 21, 2012 | |
| INVENTOR(S) | : Thomas O'Halloran et al. | |

It is certified that error appears in the above-identified patent and that said Letters Patent is hereby corrected as shown below:

Column 1, lines 7-9 should read:

-- This invention was made with government support under grant numbers GM038784 and R01 GM054111 awarded by the National Institutes of Health. The government has certain rights in the invention. --

Signed and Sealed this

Twentieth Day of November, 2012

David J. Kappos
*Director of the United States Patent and Trademark Office*

UNITED STATES PATENT AND TRADEMARK OFFICE
CERTIFICATE OF CORRECTION

PATENT NO. : 8,246,983 B2
APPLICATION NO. : 11/515711
DATED : August 21, 2012
INVENTOR(S) : Thomas O'Halloran et al.

Page 1 of 1

It is certified that error appears in the above-identified patent and that said Letters Patent is hereby corrected as shown below:

In the Specification

Column 1, Lines 7-9 should read:
-- This invention was made with government support under grant numbers GM038784, GM054111, U54 CA119341 awarded by the National Institutes of Health. The government has certain rights in the invention. --

This certificate supersedes the Certificate of Correction issued November 20, 2012.

Signed and Sealed this
Eighth Day of October, 2024

Katherine Kelly Vidal
*Director of the United States Patent and Trademark Office*